United States Patent [19]

Reed et al.

[11] Patent Number: 5,891,620
[45] Date of Patent: Apr. 6, 1999

[54] STEROID SULFATASE ASSAY

[75] Inventors: Michael J. Reed, London; Atul Purohit, South Harrow, both of Great Britain

[73] Assignee: Imperial College of Science, Technology and Medicine, London, England

[21] Appl. No.: 836,302
[22] PCT Filed: Nov. 10, 1995
[86] PCT No.: PCT/GB95/02638
  § 371 Date: Jun. 2, 1997
  § 102(e) Date: Jun. 2, 1997
[87] PCT Pub. No.: WO96/15257
  PCT Pub. Date: May 23, 1996

[30] Foreign Application Priority Data

Nov. 11, 1994 [GB] United Kingdom .................... 9422777

[51] Int. Cl.⁶ ..................................... C12Q 1/00
[52] U.S. Cl. ................................. 435/4; 435/18; 435/29; 435/183; 435/975
[58] Field of Search ................................. 435/4, 18, 29, 435/183, 975

[56] References Cited

FOREIGN PATENT DOCUMENTS

| A 0423818 | 4/1991 | European Pat. Off. . |
|---|---|---|
| A 2040043 | 8/1980 | United Kingdom . |
| WO A 9113083 | 9/1991 | WIPO . |
| WO A 9305063 | 3/1993 | WIPO . |
| WO A 9305064 | 3/1993 | WIPO . |
| 95267717 | 10/1995 | WIPO . |

OTHER PUBLICATIONS

British Journal of Dermatology, vol. 123, 1990, p. 547 XP000566526, M. Okano: "Commercial assay for steroid sulphatase activity . . . ".

J. Inherited Metabolic Disease, vol. 12, 1989, Dordrecht, pp. 273–280 XP000566527, O.P. Van Diggelen: "A Fluorometric assay of steroid sulphatase . . . ".

Okano et al. British Journal of Dermatology vol. 113 p. 645, 1985.

*Primary Examiner*—Sheela Huff
*Attorney, Agent, or Firm*—Frommer Lawrence & Haug LLP; Thomas J. Kowalski

[57] ABSTRACT

An assay comprising determining the absence or presence of steroid sulphatase activity is described. In a preferred embodiment, the assay uses white blood cells. The assay can be used to determine if an agent is an in vitro and/or in vivo steroid sulphatase inhibitor.

8 Claims, 29 Drawing Sheets

FORMULA I

FORMULA II

FORMULA III

FORMULA IV

FORMULA V

STEROID SULFATASE ASSAY

BACKGROUND OF THE INVENTION

The present invention relates to an assay.

In particular the present invention relates to an assay for use in determining the absence or presence of steroid sulphatase activity.

Steroid precursors, or pro-hormones, having a sulphate group in the 3-position of the steroid nucleus, referred to hereinafter simply as steroid sulphates, are known to play an important part as intermediates in steroid metabolism in the human body. Oestrone sulphate and dehydroepiandrosterone (DHA) sulphate, for example, are known to play an important role as intermediates in the production, in the body, of oestrogens such as oestrone, oestradiol and oestrogenic steroids such as androstenediol.

In particular, and by way of example, oestrone sulphate is known to represent one of the major circulating oestrogen precursors particularly in post-menopausal women and oestrone sulphatase activity in breast tumours is approximately a million fold greater than that of other enzymes involved in oestrogen formation (James et al., *Steroids*, 50, 269–279 (1987)).

In addition, oestrogens such as oestrone and oestradiol, particularly the over-production thereof, are strongly implicated in malignant conditions, such as breast cancer, see *Breast Cancer, Treatment and Prognosis*: Ed. R. A. Stoll, pp. 156–172, Blackwell Scientific Publications (1986), and the control of oestrogen production is the specific target of many anti-cancer therapies, both chemotherapy and surgical, e.g. oöphorectomy and adrenalectomy.

So far as endocrine therapy is concerned, efforts have so far tended to concentrate on aromatase inhibitors, i.e. compounds which inhibit aromatase activity, which activity is involved in the conversion of androgens such as androstenedione and testosterone to oestrone and oestradiol respectively.

In WO 91/13083, WO 93/05063 and WO 93/05064 are reported methods, including compounds and compositions for use in those methods, for inhibiting or at least reducing steroid sulphatase activity.

In this regard, WO 91/13083 discloses a method of targeting a different point in the oestrogen metabolic pathway, or rather two different points, that is to say the conversion of DHA sulphate and oestrone sulphate to DHA and oestrone, respectively, by steroid sulphatase activity, and using 3-monoalkylthiophosphonate steroid esters as a steroid sulphatase inhibitor, more especially oestrone-3-monomethylthiophosphonate.

WO 93/05063 discloses novel compounds, including pharmaceutically acceptable salts thereof, having steroid sulphatase inhibitory activity. These compounds are the sulphonate and phosphonate esters of polycyclic alcohols, being polycyclic alcohols the sulphate of which is a substrate for enzymes having steroid sulphatase activity. In their broadest sense, the novel compounds have the formula shown as FORMULA I in FIG. 1—wherein: R is selected from H, alkyl, cycloalkyl, alkenyl and aryl; X is P or S; Y is —OH when X is P, and =O when X is S; and the group O-Polycycle represents the residue of a polycyclic alcohol, the sulphate of which is a substrate for enzymes having steroid sulphatase activity.

WO 93/05064 discloses novel compounds, including pharmaceutically acceptable salts thereof, having steroid sulphatase inhibitory activity, and in some cases with extremely high activity levels. These compounds are the sulphamic acid esters of polycyclic alcohols, being polycyclic alcohols the sulphate of which is a substrate for enzymes having steroid sulphatase (EC 3.1.6.2) activity, the N-alkyl and N-aryl derivatives of those sulphamic acid esters. In their broadest sense, the novel compounds of WO 93/05064 have the formula shown as FORMULA II in FIG. 2a—wherein: $R_1$ and $R_2$ are each independently selected from H, alkyl, cycloalkyl, alkenyl and aryl, or together represent alkylene optionally containing one or more hetero atoms or groups in the alkylene chain; and the group —O—Polycycle represents the residue of a polycyclic alcohol, the sulphate of which is a substrate for enzymes having steroid sulphatase activity (EC 3.1.6.2).

In WO 93/05063 and WO 93/05064 the reference to polycyclic alcohols, the sulphate of which is a substrate for enzymes having steroid sulphatase activity, refers to polycyclic alcohols of the formula shown as FORMULA III in FIG. 2b—which when incubated with steroid sulphatase EC 3.1.6.2 at pH 7.4 and 37° C., provides a $K_m$ value of less than 50 μmoles/l.

The compositions of WO 91/13083, WO 93/05063 and WO 93/05064 are capable of inhibiting steroid sulphatase activity in vitro and in vivo, have improved activity as steroid sulphatase inhibitors both in vitro and in vivo, provide pharmaceutical compositions effective in the treatment of oestrogen dependent tumours, provide pharmaceutical compositions effective in the treatment of breast cancer, enable oestrogen dependent tumours in mammals, especially humans, to be treated and enable breast cancer in mammals and especially in women to be treated.

U.S. Pat. No. 4,150,126 proposes for use as antitumour agents steroid enol esters of the formula shown as FORMULA IV in FIG. 3a—where: PH is a phenyl group, $R^1$ is ($C_2$–$C_4$) β- or γ-haloalkyl; $R^2$ is H, lower alkyl, lower alkoxy or halogen; A provides a $C_1$–$C_4$ hydrocarbon chain between —C(O)— and X; X is O or S; k and m=0 or 1, with the proviso that when m=1 then k=1; and St is a steroid skeleton to which the ester group is attached at the 3-position and adjacent a double bond in the steroid A ring. However no mechanistic explanation is given of the antitumour activity of those compounds.

In U.S. Pat. No. 4,150,126 a brief mention is made that such steroid and esters can be prepared by transesterification inter alia of steroid-3-sulphonates of the formula shown as FORMULA V in FIG. 3b—wherein St is a steroid nucleus as above defined, and $R^3$ is lower alkyl, optionally containing chloro- or fluoro-substituents, or phenyl, optionally substituted by chloro-, fluoro- or lower alkyl.

However, no examples are given of any such steroid-3-sulphonates for use as intermediates in the preparation of the described steroid enol esters, let alone any suggestion that such steroid-3-sulphonates might themselves inhibit steroid sulphatase activity, and thus be of potential value in the treatment of oestrogen dependent tumours.

There is therefore a need to have a reliable assay to determine whether or not an agent, which may be a compound or a composition, would be effective as a steroid sulphatase inhibitor. Such an assay would enable agents to be screened easily and effectively for potential clinical use.

There is also a need to have a reliable assay to determine whether or not an agent, which may be a compound or a composition, has reduced or eliminated steroid sulphatase activity after the agent has been administered to a subject—e.g. a patient.

Furthermore, the existing procedures to determine the in vivo effectiveness of such agents require harsh invasive techniques such as surgery to inspect the extent of tumour regression. This is clearly unacceptable if the long term or continual action of an agent needs to be monitored.

The present invention seeks to provide a reliable assay to determine the extent of steroid sulphatase inhibition and, furthermore, to overcome the problems associated with the known methods.

SUMMARY OF THE INVENTION

According to a first aspect of the present invention there is provided an assay method for determining the level (e.g. absence or presence, including measuring the activity levels thereof) of steroid sulphatase activity of a sulphatase type enzyme usually associated with white blood cells comprising exposing the sulphatase type enzyme to a reagent that can indicate steroid sulphatase activity.

According to a second aspect of the present invention there is provided an assay kit comprising a sulphatase type enzyme usually associated with white blood cells and a reagent that can indicate steroid sulphatase activity.

According to a third aspect of the present invention there is provided an assay comprising a sulphatase type enzyme usually associated with white blood cells, a reagent that can indicate steroid sulphatase activity and an agent for testing as a steroid sulphatase inhibitor.

The term "sulphatase type enzyme" includes an enzyme possessing sulphatase activity.

The term "sulphatase activity" preferably means having a steroid sulphatase activity in accordance with classification number EC 3.1.6.2.

The term "associated" includes the sulphatase type enzyme being linked or joined (e.g. by electrostatic, covalent, ionic or hydrogen bonds) to one or more white blood cells.

The term "white blood cells" includes natural white blood cells and variants thereof, such as modified white blood cells.

The term "sulphatase type enzyme usually associated with white blood cells" includes a sulphatase type enzyme normally associated with white blood cells when present in whole blood. However, for the main aspects of the present invention the sulphatase type enzyme can be dissociated from white blood cells (i.e. in isolated form) or it can be associated with the white blood cells (i.e. still in associated form), which in turn need not be isolated from whole blood.

Preferably the reagent is $^{14}$C-E$_1$S and/or $^3$H-E$_1$S, wherein the absence or presence of steroid sulphatase activity is indicated by the respective absence or presence of $^{14}$C-E$_1$ or $^3$H-E$_1$, respectively. E$_1$S is oestrone sulphate and E$_1$ is oestrone.

In one preferred embodiment, the sulphatase type enzyme is exposed in vitro to an agent in order to determine if that agent is a steroid sulphatase inhibitor.

In another preferred embodiment, the steroid sulphatase type enzyme has been extracted from a subject after an agent has been administered to the subject in order to determine if that agent is a steroid sulphatase inhibitor.

In another preferred embodiment, the steroid sulphatase type enzyme has been extracted from a subject (not necessarily after an agent has been administered to the subject) in order to determine the in vivo level of steroid sulphatase activity.

Preferably the agent is or comprises an irreversible or, preferably, a reversible steroid sulphatase inhibitor.

Preferably the agent is or comprises a compound covered by WO 91/13083, WO 93/05063 or WO 93/05064.

Preferably the compound is a sulphamate of Formula II.

Preferably the compound is oestrone-3-sulphamate or oestrone-3-N,N-dimethylsulphamate.

More preferably the compound is oestrone-3-sulphamate.

The present invention is based on the surprising finding that the sulphatase type enzyme naturally associated with white blood cells can be used in an assay to determine the level of steroid sulphatase inhibition by an agent, which may be a compound or a composition.

Even more surprising findings are that the sulphatase type enzyme need not be dissociated from the white blood cells and that the sulphatase type enzyme when still associated with the white blood cells need not be isolated from whole blood.

The advantages of the present invention are that it provides a reliable assay, the sulphatase type enzyme is easy to extract from a subject—for example by extracting whole blood from a subject (e.g. a patient) by use of a needle and syringe, the enzyme need not be purified from the whole blood, the enzyme need not be dissociated from white blood cells, the assay can be used to screen easily and effectively agents prior to clinical use, the assay does not include the use of harsh invasive techniques (at most it involves the use of a needle and syringe) and the assay can be used to determine easily the effectiveness of agents after they have been administered to a subject.

The last mentioned advantage is very important for clinical studies, trials and treatments.

For example, the present invention allows a course of treatment to be easily monitored, provides an indication if a particular treatment ought to be continued or stopped, enables one to study sulphatase abnormalities.

Another important use of the assay of the present invention concerns irreversible and/or "suicide" inhibitors. In this regard, in conventional drug testing the dose of a drug to be used clinically is established by direct measurement of efficacy. The minimum level of drug associated with the efficacious response is then noted. The dosing regimen is then worked out by considering the pharmacokinetics of the drug in plasma, organ or wherever is appropriate for the pharmacological response and determining how frequently the drug needs to be administered to maintain the drug at a therapeutic concentration at its site of action. This is then checked by monitoring drug levels following repeated administration. This reliance on measurement of drug levels is clearly inappropriate in the case of irreversible agents. In these circumstances the proportionality between drug level and response does not exist. With those agents, therefore, the only way of establishing what would be a suitable dosing interval is by way of measuring sulphatase activity as an temporal index of the action of the drug. The assay of the present inventions lends itself well to such an application.

Furthermore, in some instances, quantification of the action of an agent (drug) is an improvement over the quantification of the presence of a drug, not only in determining these factors for an irreversible agent but also for a reversible agent.

In summation, the present invention therefore provides an assay for determining easily and effectively if an agent is an in vitro and/or in vivo steroid sulphatase inhibitor.

As the sulphatase type enzyme need not be dissociated from the white blood cells (i.e. the sulphatase type enzyme can still be associated with the white blood cells), and wherein the sulphatase type enzyme and the white blood cells can be present in whole blood or isolated therefrom, highly preferred embodiments of the present invention include:

an assay method for determining the level (e.g. the absence or presence) of steroid sulphatase activity of a sulphatase type enzyme still associated with white blood cells comprising exposing the sulphatase type enzyme to a reagent that can indicate steroid sulphatase activity;

an assay method comprising exposing a sulphatase type enzyme still associated with white blood cells in vitro to an agent in order to determine if that agent is a steroid sulphatase inhibitor;

an assay method comprising measuring the level of steroid sulphatase activity of a sulphatase type enzyme still associated with white blood cells wherein the white blood cells and the sulphatase type enzyme have been extracted from a subject after an agent has been administered to the subject in order to determine if that agent is an in vivo steroid sulphatase inhibitor;

an assay kit comprising a sulphatase type enzyme still associated with white blood cells and a reagent that can indicate steroid sulphatase activity;

an assay comprising a sulphatase type enzyme still associated with white blood cells, a reagent that can indicate steroid sulphatase activity and an agent for testing as a steroid sulphatase inhibitor.

In another embodiment the present invention relates to a chemical compound or chemical composition when screened by use of the assay (or assay method or assay kit) of the present invention.

BRIEF DESCRIPTION OF THE DRAWINGS

The present invention will now be described only by way of example, in which reference shall be made to FIGS. 1–30; which Figures are now discussed.

DETAILED DESCRIPTION OF THE INVENTION

First Method

An agent is added, in an appropriate amount, to any one of the assay media described below. The level of sulphatase activity is then determined in order to find out if the agent is an effective in vitro sulphatase inhibitor.

Second Method

A body extract (e.g. blood) from a subject (e.g. a patient) containing a pre-administered agent (such as oestrone-3-sulphamate or oestrone-3-N,N-dimethylsulphamate) is added, in an appropriate amount, to any one of the assay media described below. The level of sulphatase activity is then determined in order to find out if the agent is an effective in vivo sulphatase inhibitor.

Third Method

A body extract (e.g. blood) from a subject (e.g. a patient) not necessarily containing a pre-administered agent (such as oestrone-3-sulphamate or oestrone-3-N,N-dimethylsulphamate) is added, in an appropriate amount, to any one of the assay media described below. The level of sulphatase activity is then determined in order to find out if there has been adequate suppression of sulphatase activity.

Assay 1

Whole Blood Est Assay

Fresh whole heparinised blood (0.5 ml) is incubated with $^3$H-E$_1$S (2 nM, 2×10$^5$ dpm) and $^{14}$C-E$_1$ (5×10$^3$ dpm) at 37° C. in a final volume of 1 ml of 2–20 hrs.

Assay 2

White Blood Cell Est Assay (Partially Purified)

Heparinised blood (10 ml) is centrifuged at 1500 rpm for 10 min. The plasma is discarded. The 'buffy' layer of white cells is then pipetted (with as little contamination as possible with r.b.c.), and incubated as above in a final volume of 1 ml for 2 hrs at 37° C.

Assay 3

White Blood Cell Est Assay

Purified leukocytes (according to Tulchinsky JCEM 65, 1026, 1987) from 10 ml whole blood are suspended in 1 ml PBS-sucrose. 0.2 ml of this is used for EST assay as above (incubated for 2 hr at 37° C. in a final volume of 1 ml).

After incubation, samples are extracted with 4 ml toluene. 2 ml of this is counted in 10 ml Scintillant.

If the crude or purified leukocytes are sonicated, then 20 μM $^3$H-E$_1$S could be added and incubated for 1 hr.

Assay 4

Isolated Sulphatase Type Enzyme Assay

Leukocytes from 10 ml whole blood are suspended in 1 ml PBS-sucrose. 0.2 ml of this is used for EST assay as above (incubated for 2 hr at 37° C. in a final volume of 1 ml). After incubation, samples are extracted with 4 ml toluene. 2 ml of this is counted in 10 ml Scintillant.

The sulphatase type enzyme is then isolated from the remaining leukocytes by appropriate means—such as via chemical cleavage and subsequent separation using, for example, a gel. The isolated sulphatase type enzyme is then incubated as above.

Rat Studies

The assay of the present invention, as described above, was investigated using rats. The details and results of those studies are shown in the attached FIGS. 5–29, which have been discussed above. The results show that the assay of the present invention is of benefit to assess steroid sulphatase activity.

Human Studies

Figure 30:
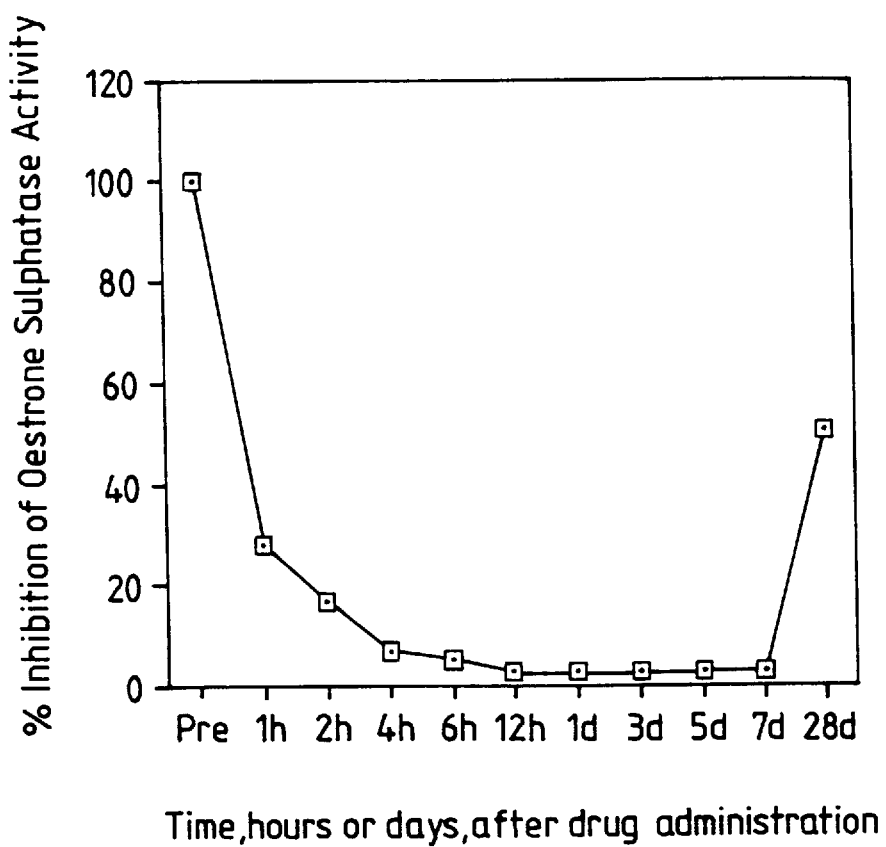
FIG. 30 is a graph of oestrone sulphatase activity in WBC of healthy male volunteers at various time intervals following single oral administration of E-Mate (0.5 mg/kg).

The assay of the present invention, as described above, was investigated using two healthy, male volunteers whom received an oral dose of a steroid sulphatase inhibitor (Oestrone-3-O-sulphamate, 0.5 mg/Kg). In this regard, white blood cells were prepared from blood samples obtained from the subjects for up to 28 days. The assay of Oestrone sulphatase activity in these cells revealed significant inhibition. The results from this study confirm that the measurement of Oestrone Sulphatase activity in white blood cells will therefore allow the extent and duration of sulphatase inhibition to be monitored in subjects receiving steroid sulphatase inhibitors therapeutically. More details and results of these studies are shown in the attached FIG. 30. The results show that the assay of the present invention is of benefit to assess steroid sulphatase activity. In particular, the assay of the present invention allows one to measure oestrone sulphatase activity in human white blood cells to monitor the extent of oestrone sulphatase inhibition.

Other modifications of the present invention will be apparent to those skilled in the art.

We claim:

1. An assay method for determining the level of steroid sulphatase activity of a sulphatase enzyme associated with white blood cells when present in whole blood and thereby determining if an agent is an effective in vivo sulphatase inhibitor, the assay method comprising the steps of:

administering the agent to a subject and extracting sulphatase enzyme from the subject;

exposing the sulphatase enzyme to a substrate that indicates steroid sulphatase activity;

determining the level of steroid sulphatase activity of the sulphatase enzyme; and thereby determining if the agent is an effective in vivo sulphatase inhibitor.

2. The method of claim 1, wherein the substrate is selected from the group consisting of $^{14}$C-E$_1$S, $^3$H-E$_1$S and mixtures thereof.

3. The method of claim 1, wherein the agent comprises an irreversible or a reversible steroid sulphatase inhibitor.

4. The method of claim 3, wherein the agent comprises a reversible steroid sulphatase inhibitor.

5. The method of claim 1 wherein the agent is an irreversible or a reversible steroid sulphatase inhibitor.

6. The method of claim 5, wherein the agent is a reversible steroid sulphatase inhibitor.

Figure 1:
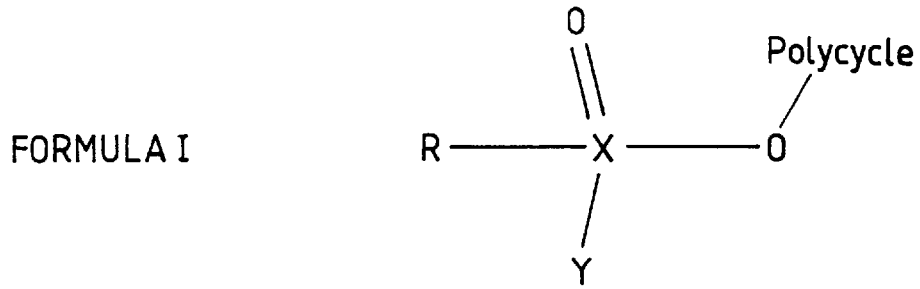
FIG. 1 shows the compounds of formula I of the invention.
Figure 2A:
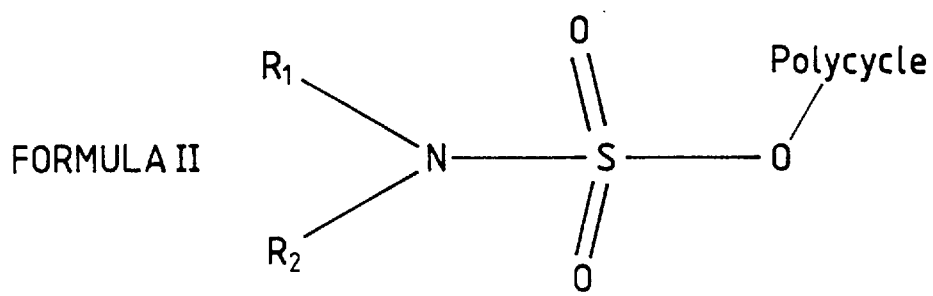
FIG. 2a shows compounds of formula II.
Figure 2B:
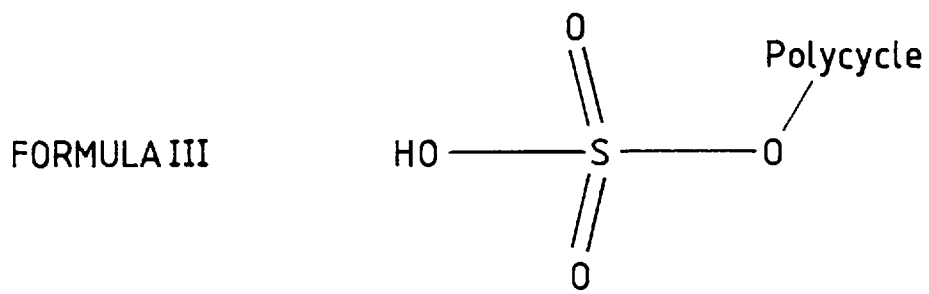
FIG. 2b shows compounds of formula III.
Figure 3A:
FIG. 3a shows compounds of formula IV.
Figure 3B:
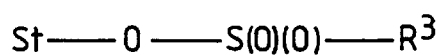
FIG. 3b shows compounds of formula V.
Figure 4:
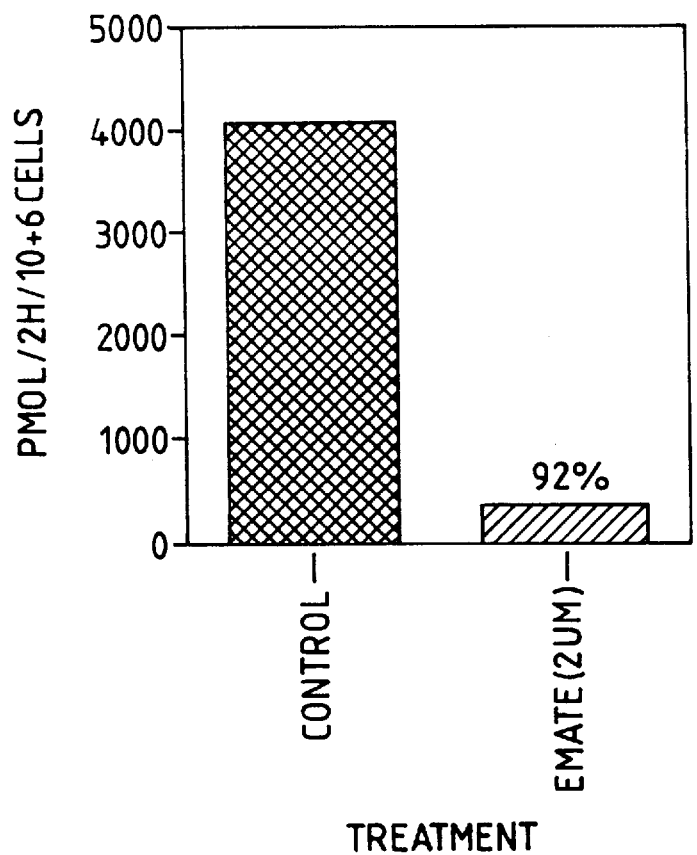
FIG. 4 is a chart showing that the sulphatase activity of the sulphatase type enzyme usually associated with blood cells is capable of indicating the sulphatase inhibition effect of oestrone-3-sulphamate ("E-MATE").
Figure 5:
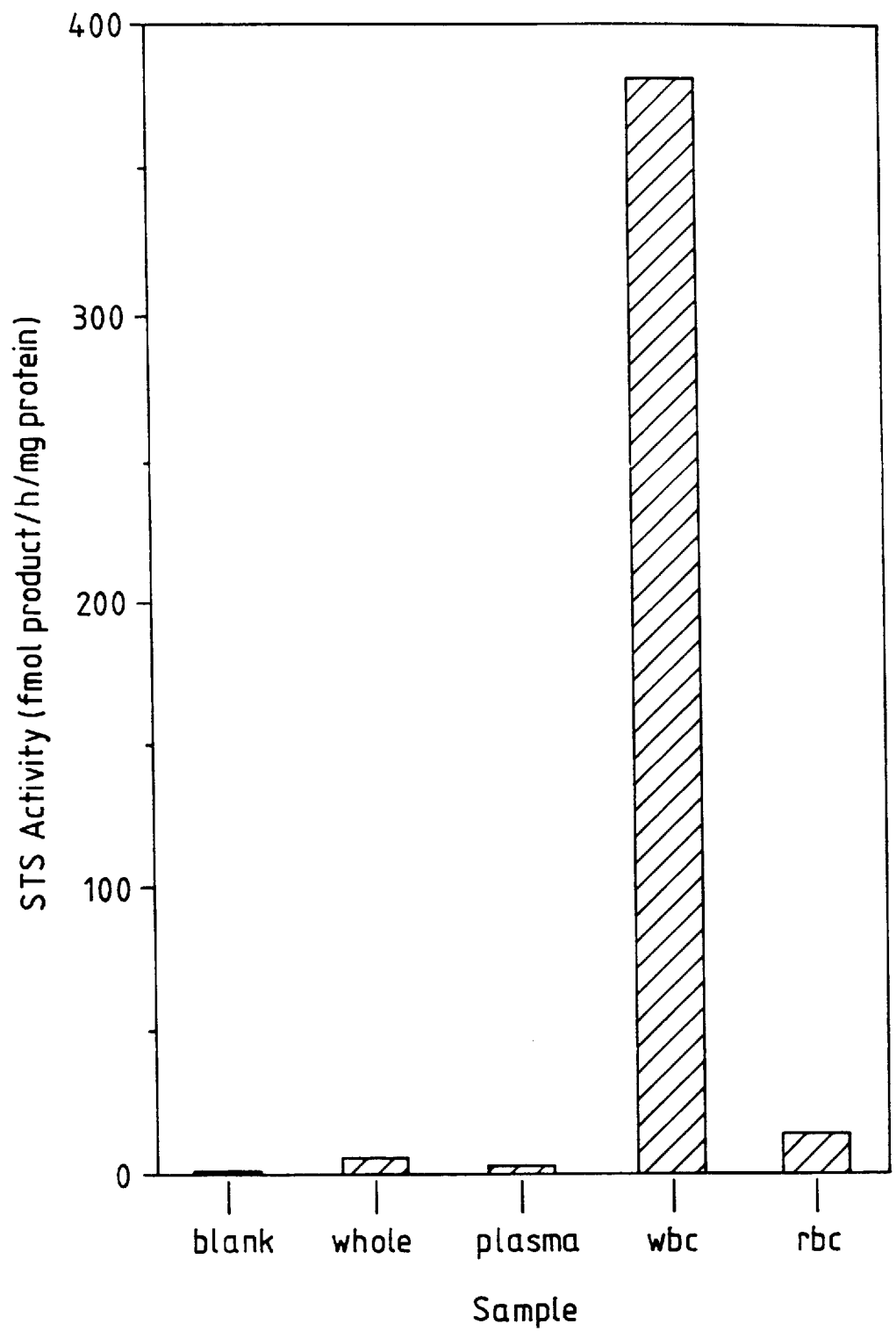
FIG. 5 is a chart of oestrone sulphatase activity in blood compartments.
Figure 6:
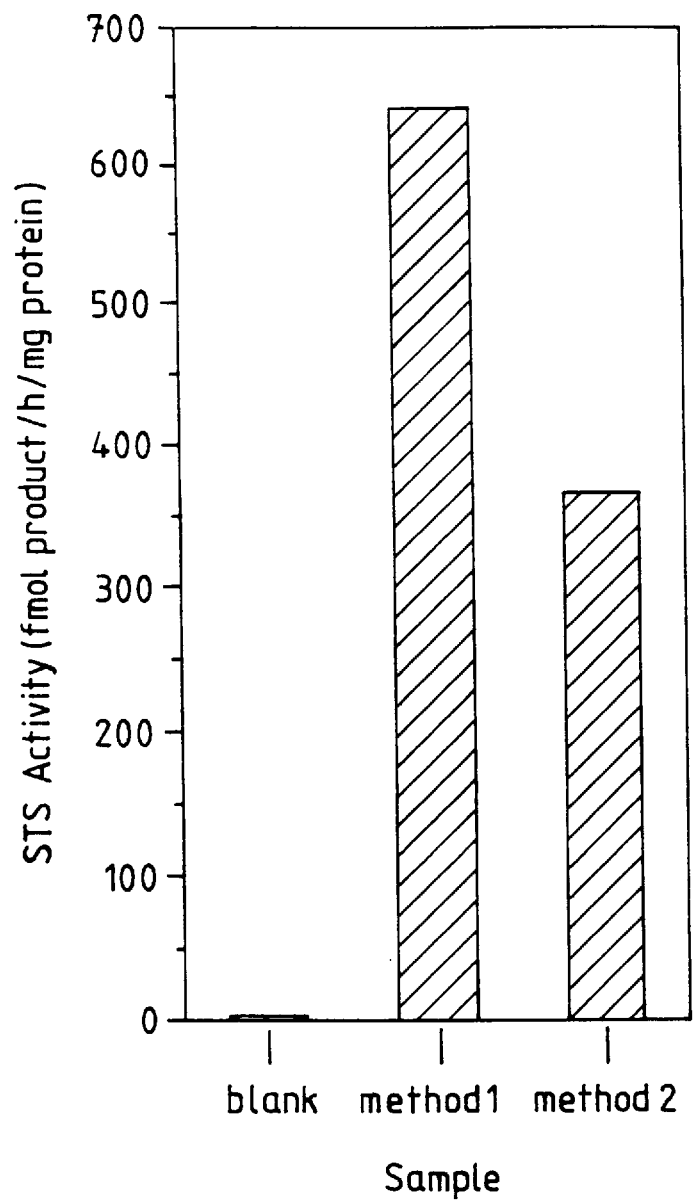
FIG. 6 is a comparison of oestrone sulphatase activity in WBC (white blood cells) prepared by method 1 and 2 (see below).
Figure 7:
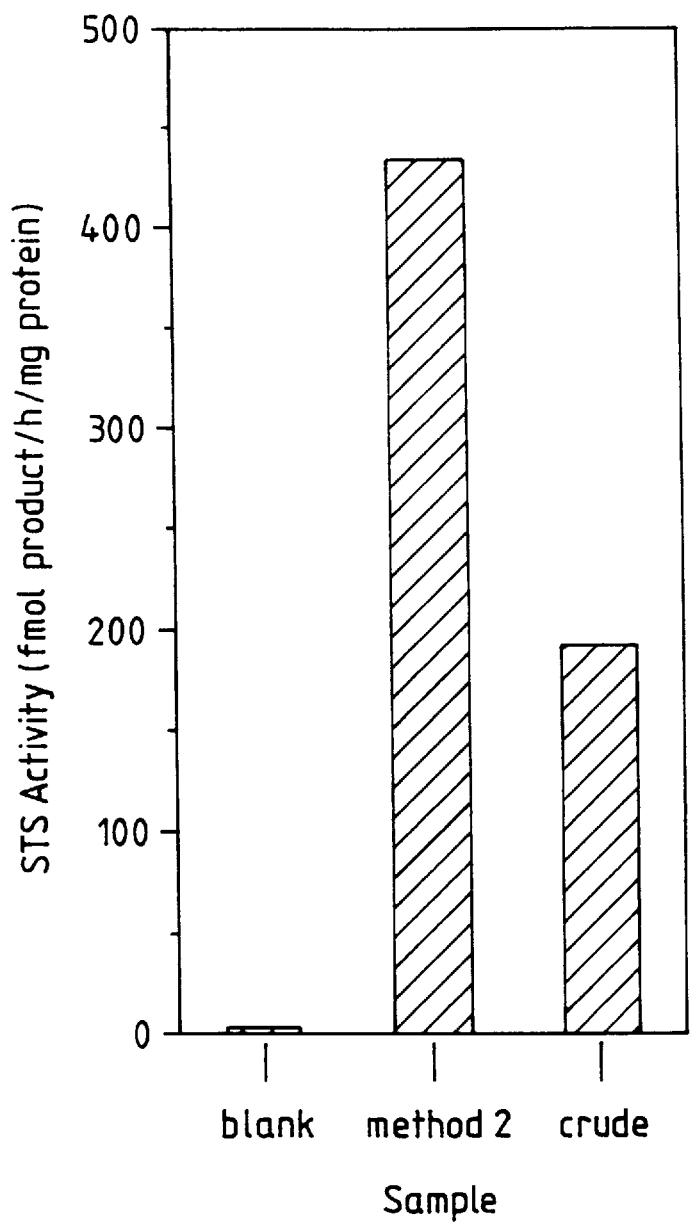
FIG. 7 is a comparison of oestrone sulphatase activity in WBC prepared by method 2 and WBC prepared more crudely.
Figure 8:
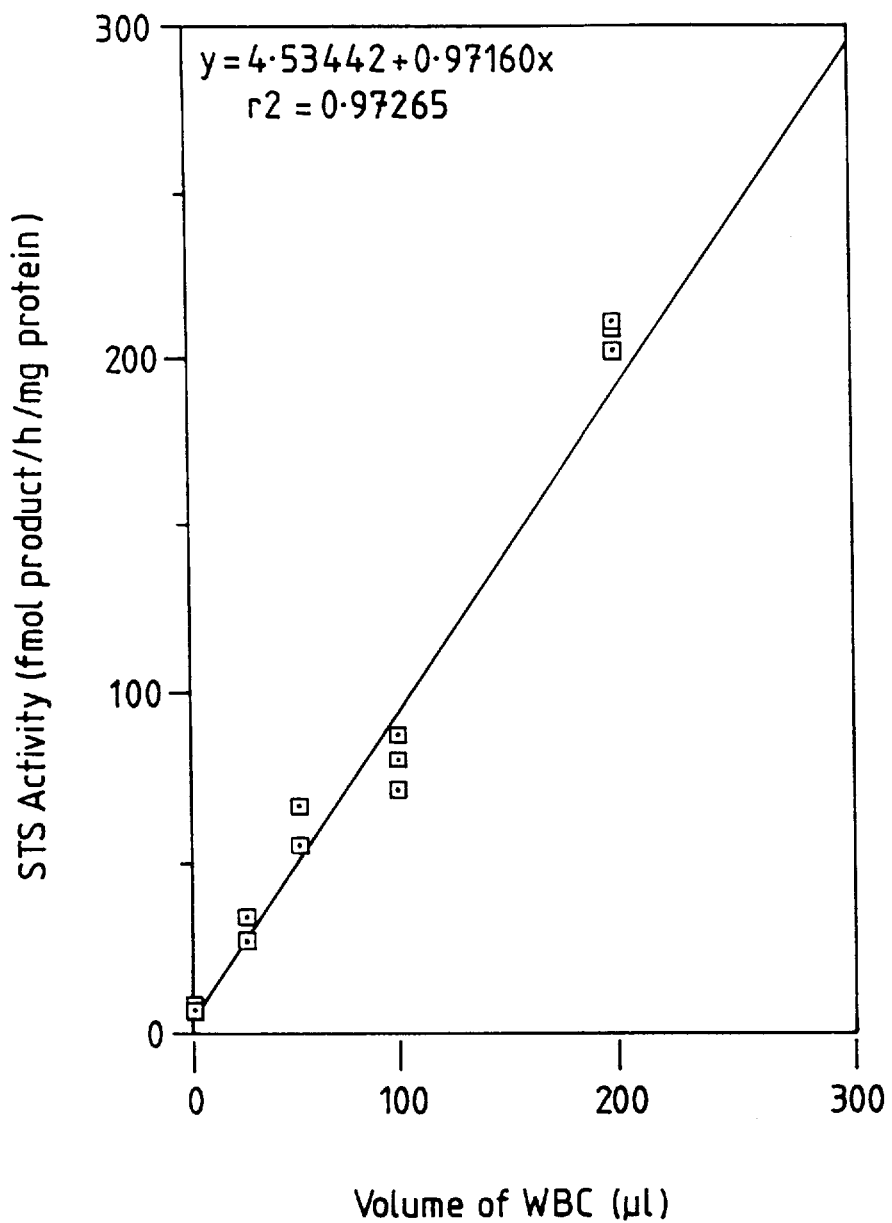
FIG. 8 is a graph of oestrone sulphatase activity in different volumes of WBC.
Figure 9:
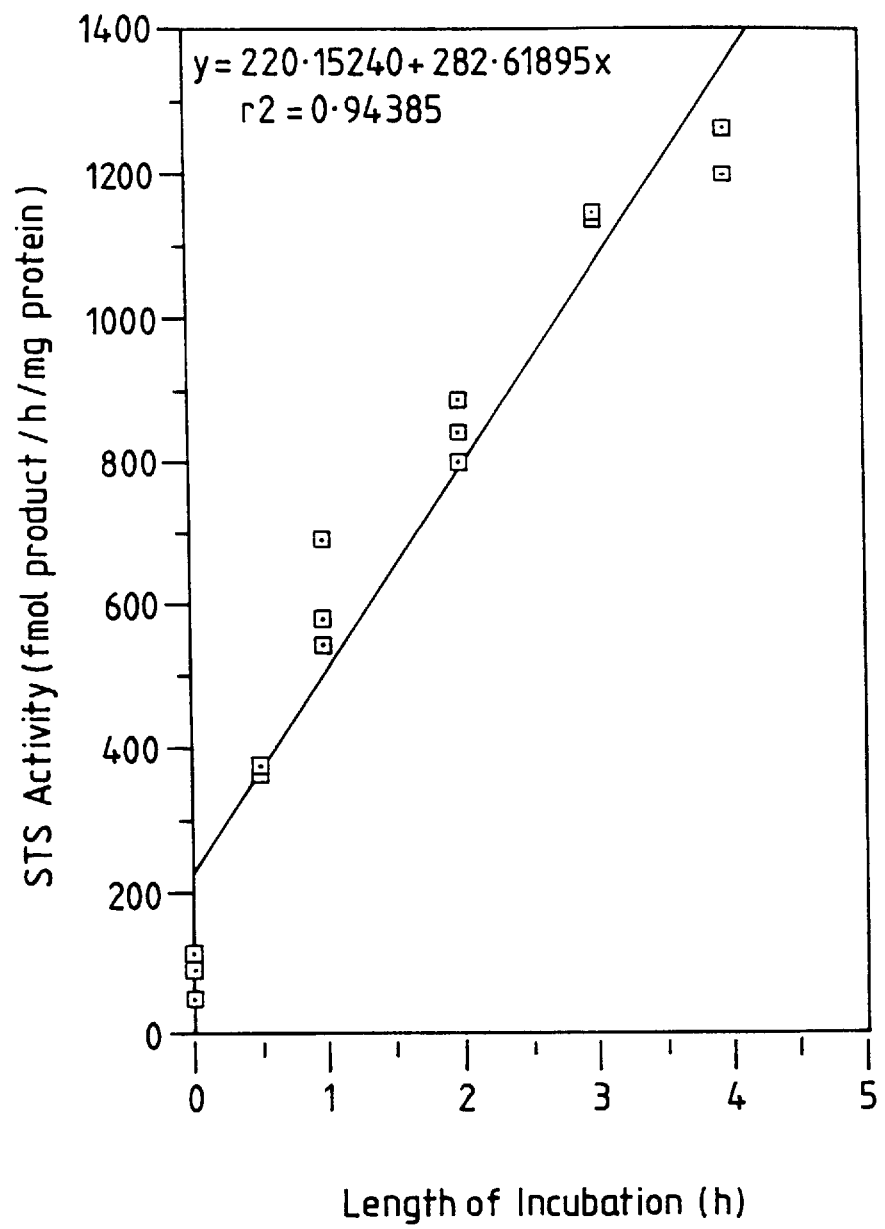
FIG. 9 is a graph of oestrone sulphatase activity in WBC incubated at 37° C. for different lengths of time.
Figure 10:
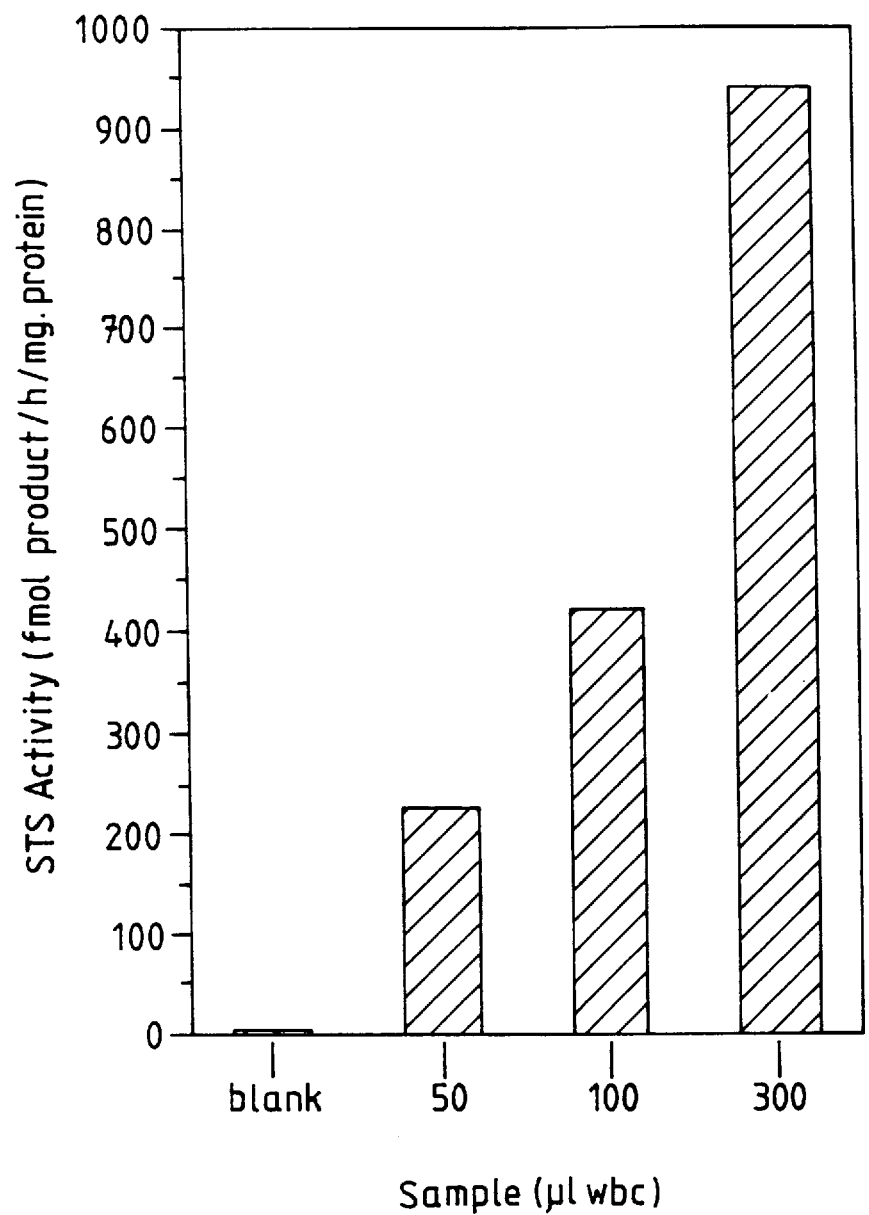
FIG. 10 is a chart of oestrone sulphatase activity in different volumes of WBC assayed fresh.
Figure 11:
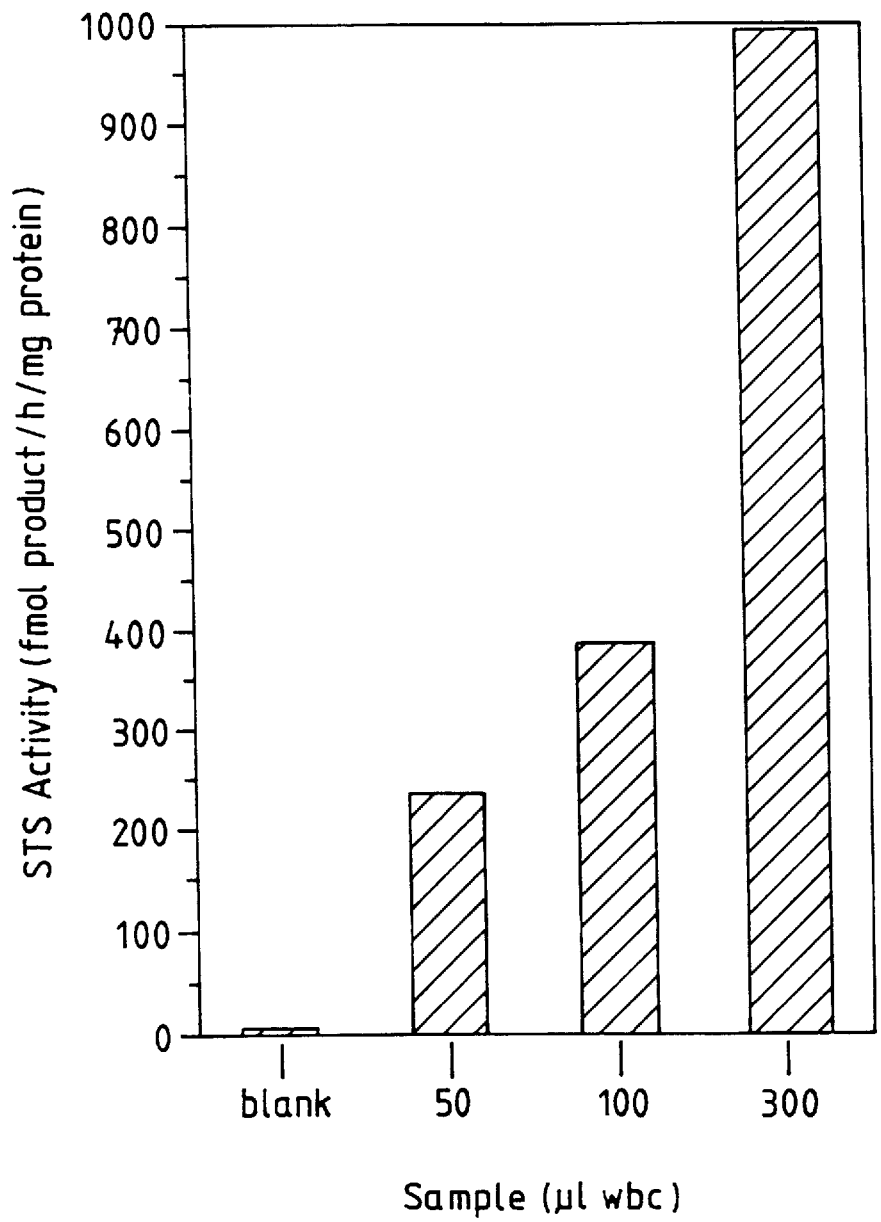
FIG. 11 is a chart of oestrone sulphatase activity in different volumes of WBC assayed after freezing and thawing.
Figure 12:
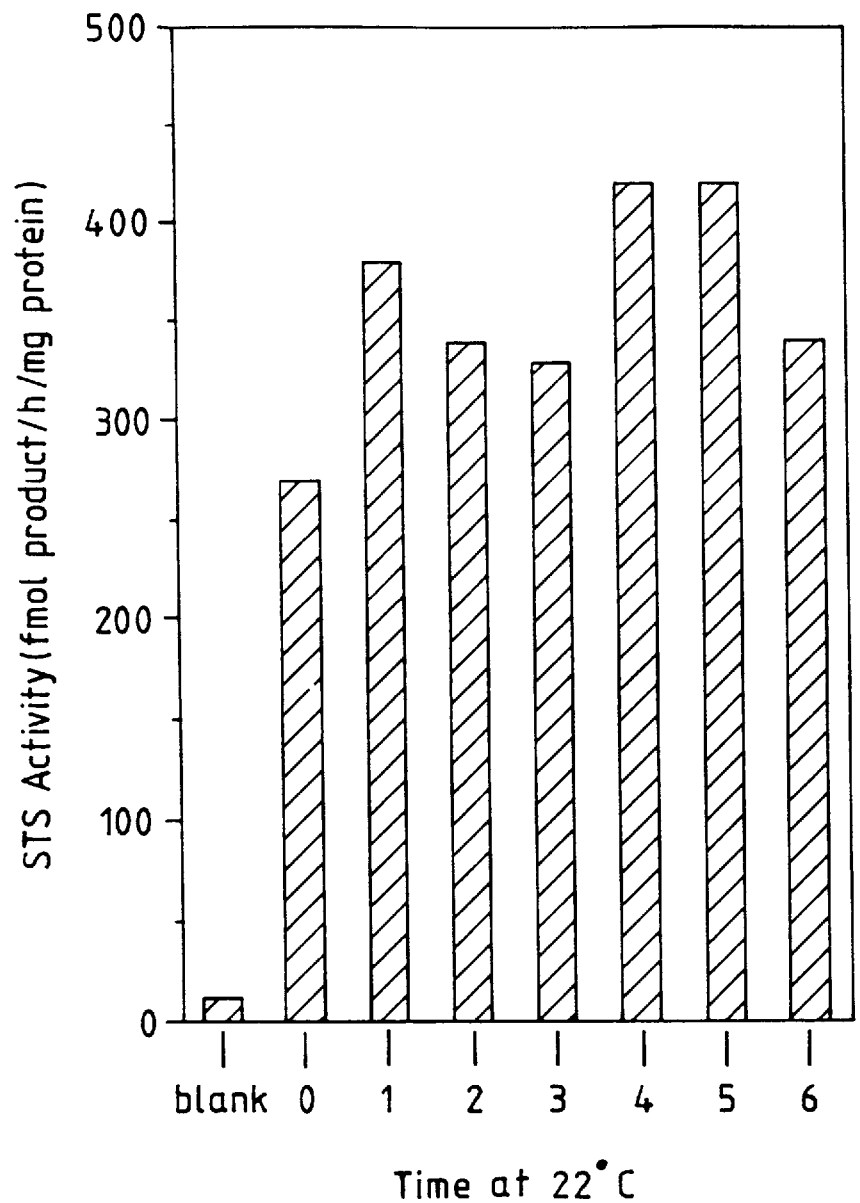
FIG. 12 is a chart of oestrone sulphatase activity in WBC after whole blood left at 22° C. for different time periods.
Figure 13:
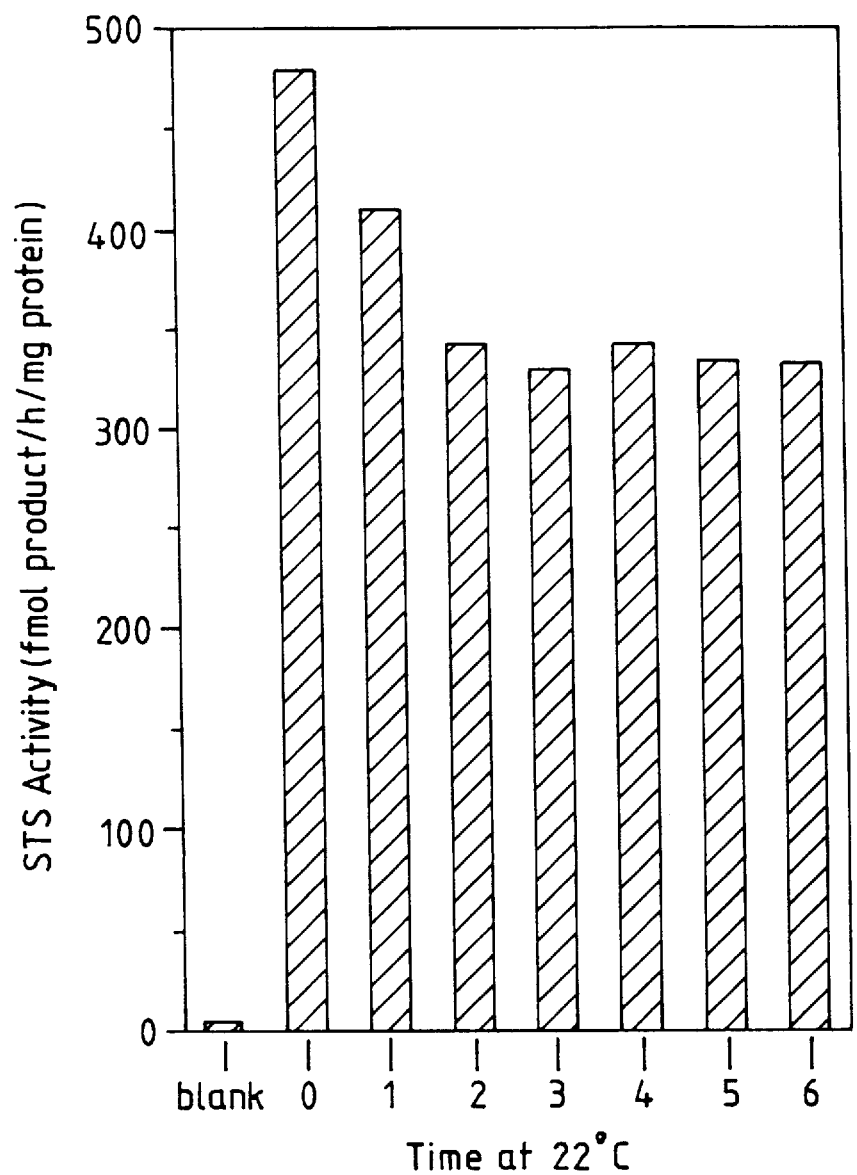
FIG. 13 is a chart of oestrone sulphatase activity in WBC after whole blood left at 22° C. for different time periods.
Figure 14:
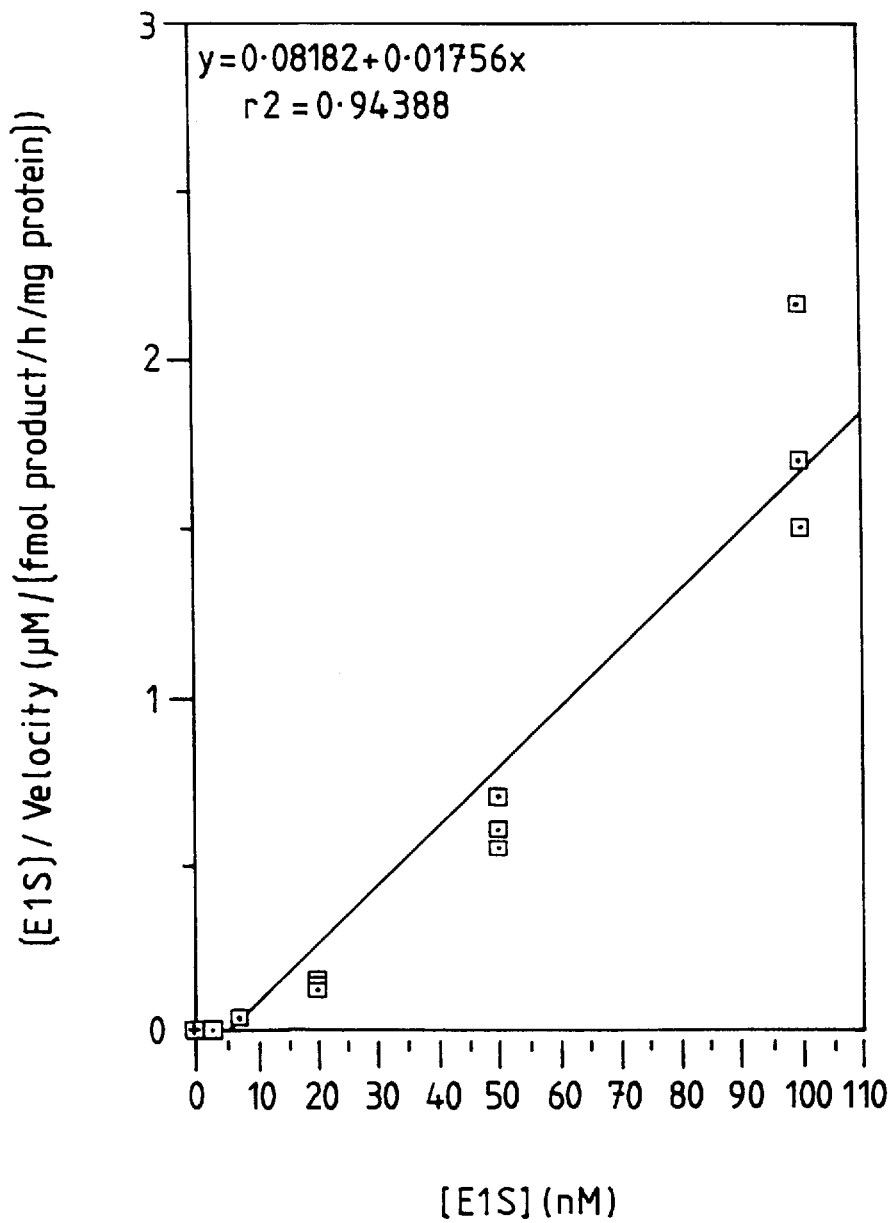
FIG. 14 is a Hane's Woolf Plot of oestrone sulphate substrate concentration against substrate concentration/velocity.
Figure 15:
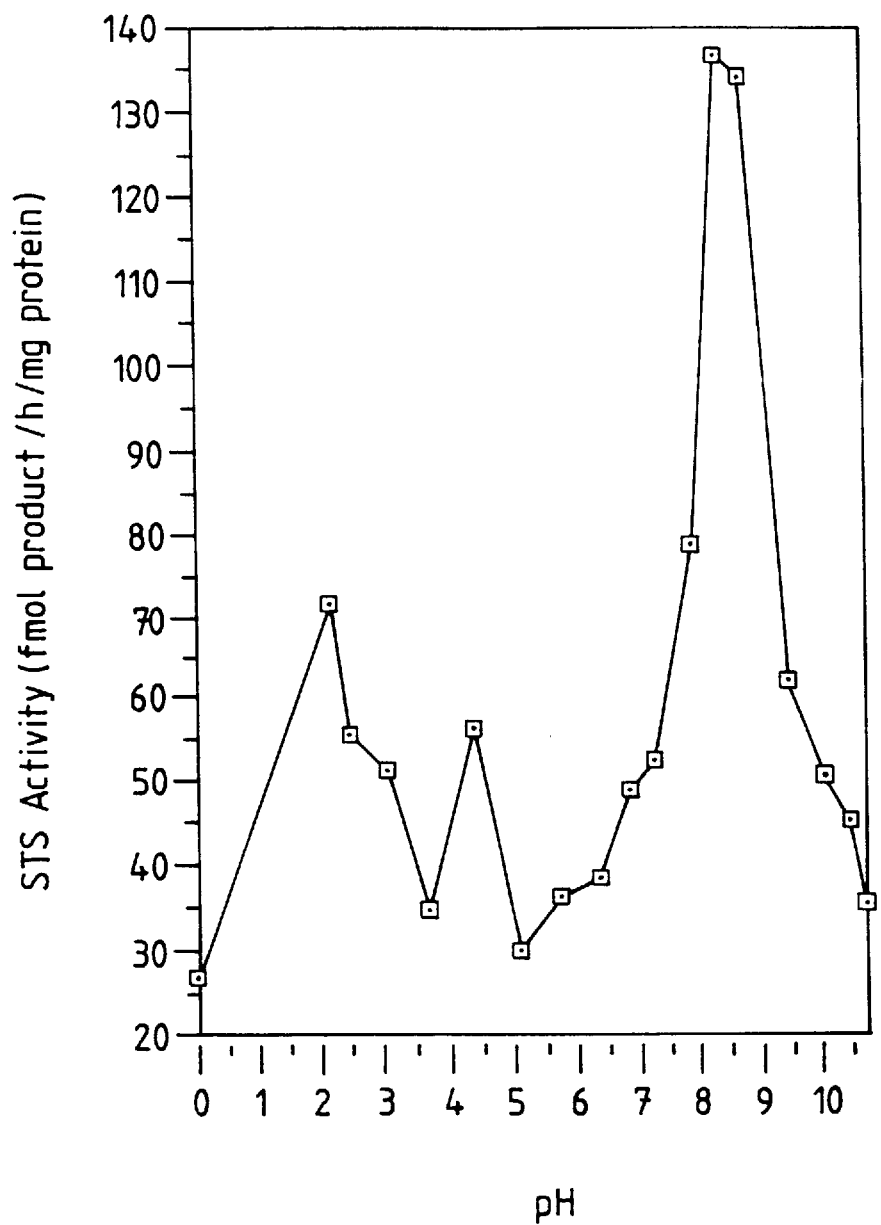
FIG. 15 is a pH profile of oestrone sulphatase activity in WBC.
Figure 16:
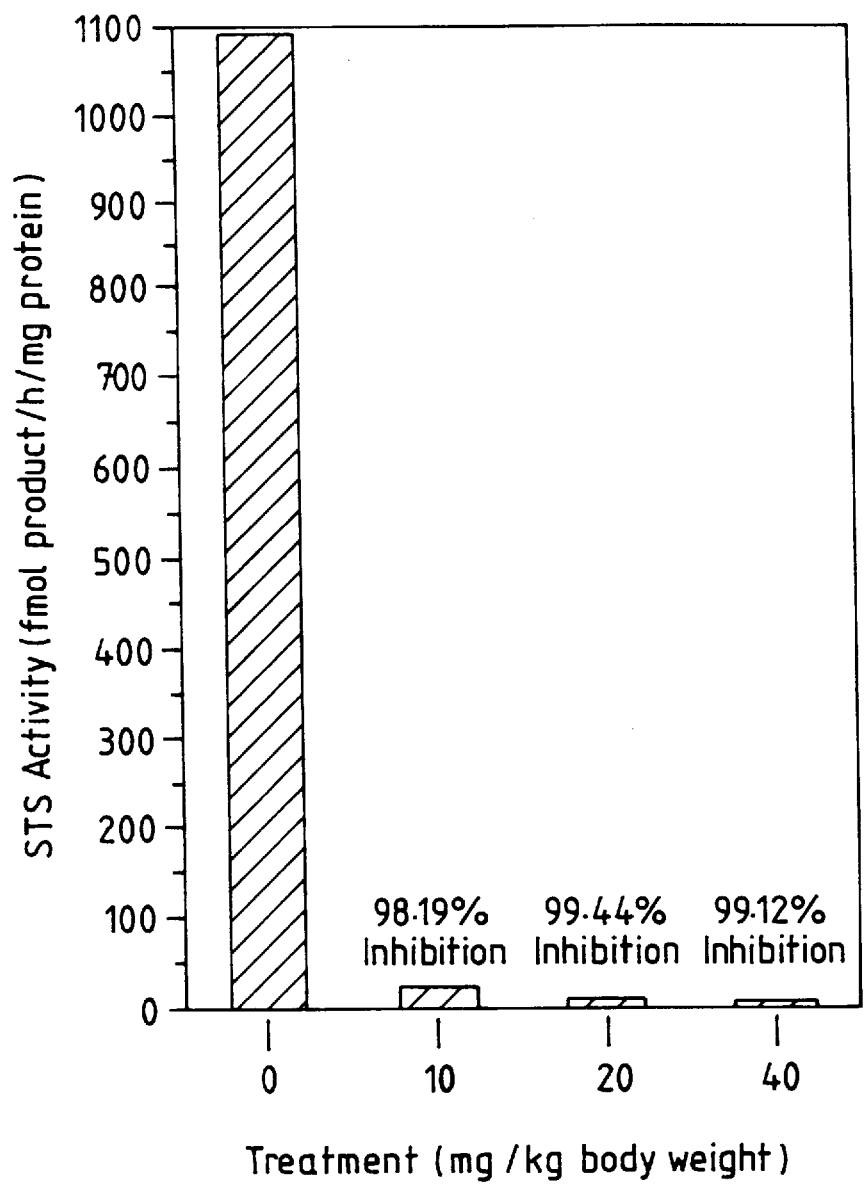
FIG. 16 is a chart of oestrone sulphatase activity in WBC of female Wistar rats two hours following single oral administration of various doses of oestrone-3-sulphamate (E-Mate).
Figure 17:
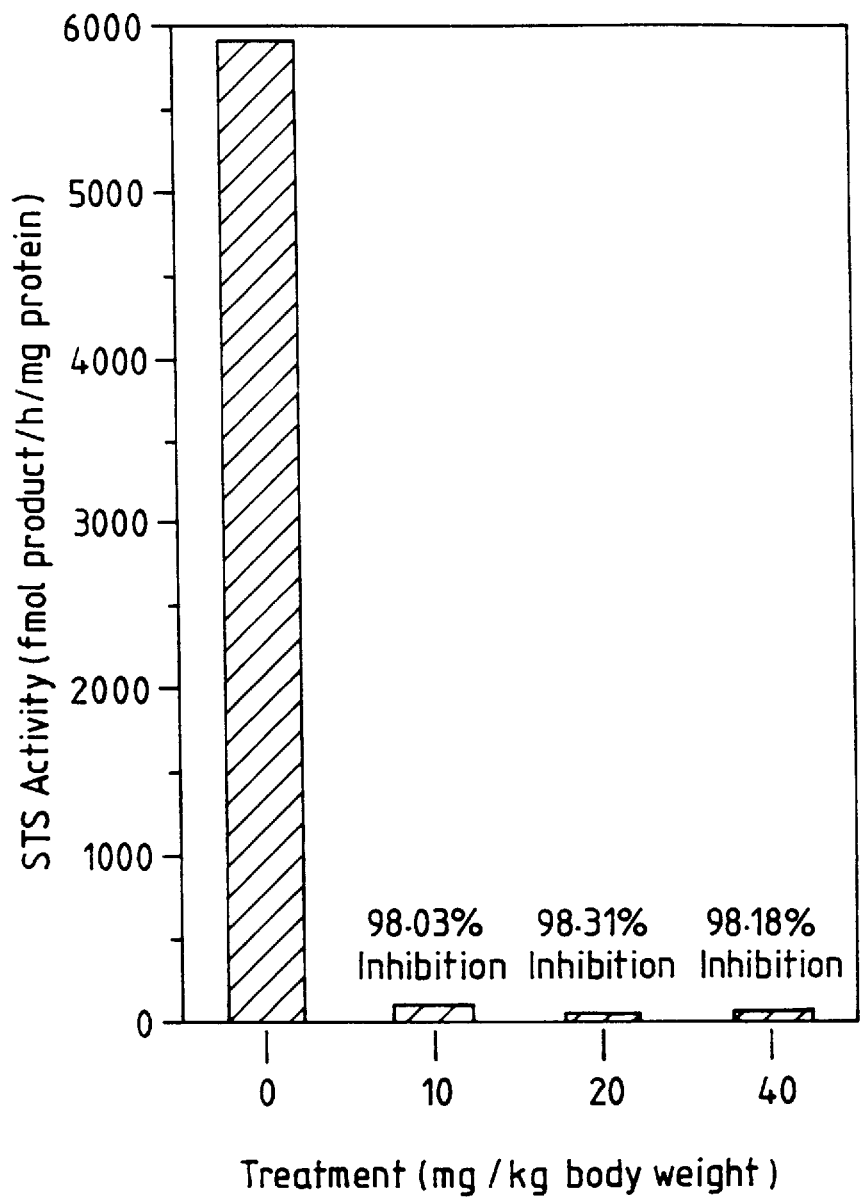
FIG. 17 is a chart of oestrone sulphatase activity in liver tissue of female Wistar rats two hours following single oral administration of E-Mate (various doses).
Figure 18:
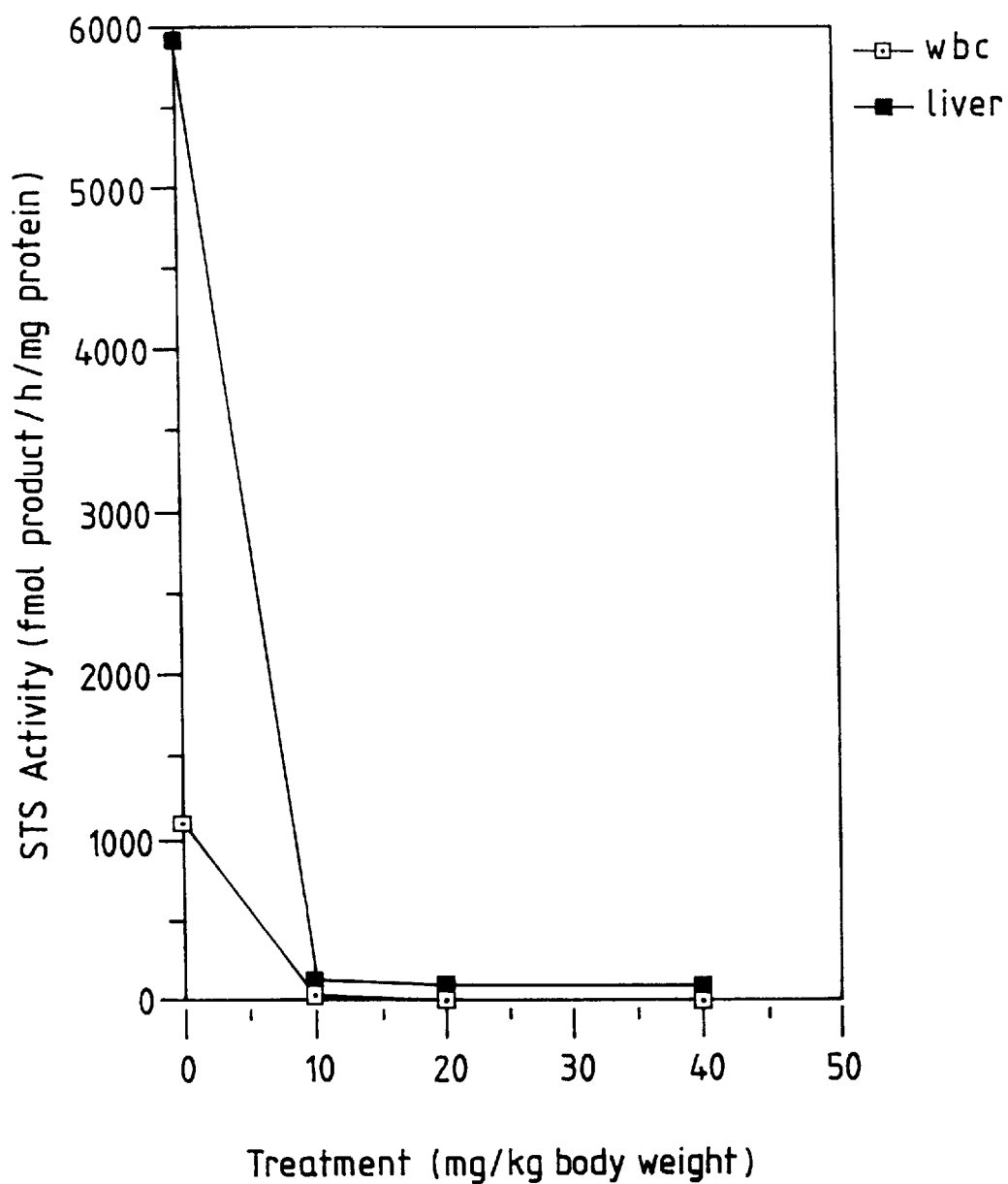
FIG. 18 is a graph of oestrone sulphatase activity in WBC and liver tissue of female Wistar rats two hours following single oral administration of E-Mate (various doses).
Figure 19:
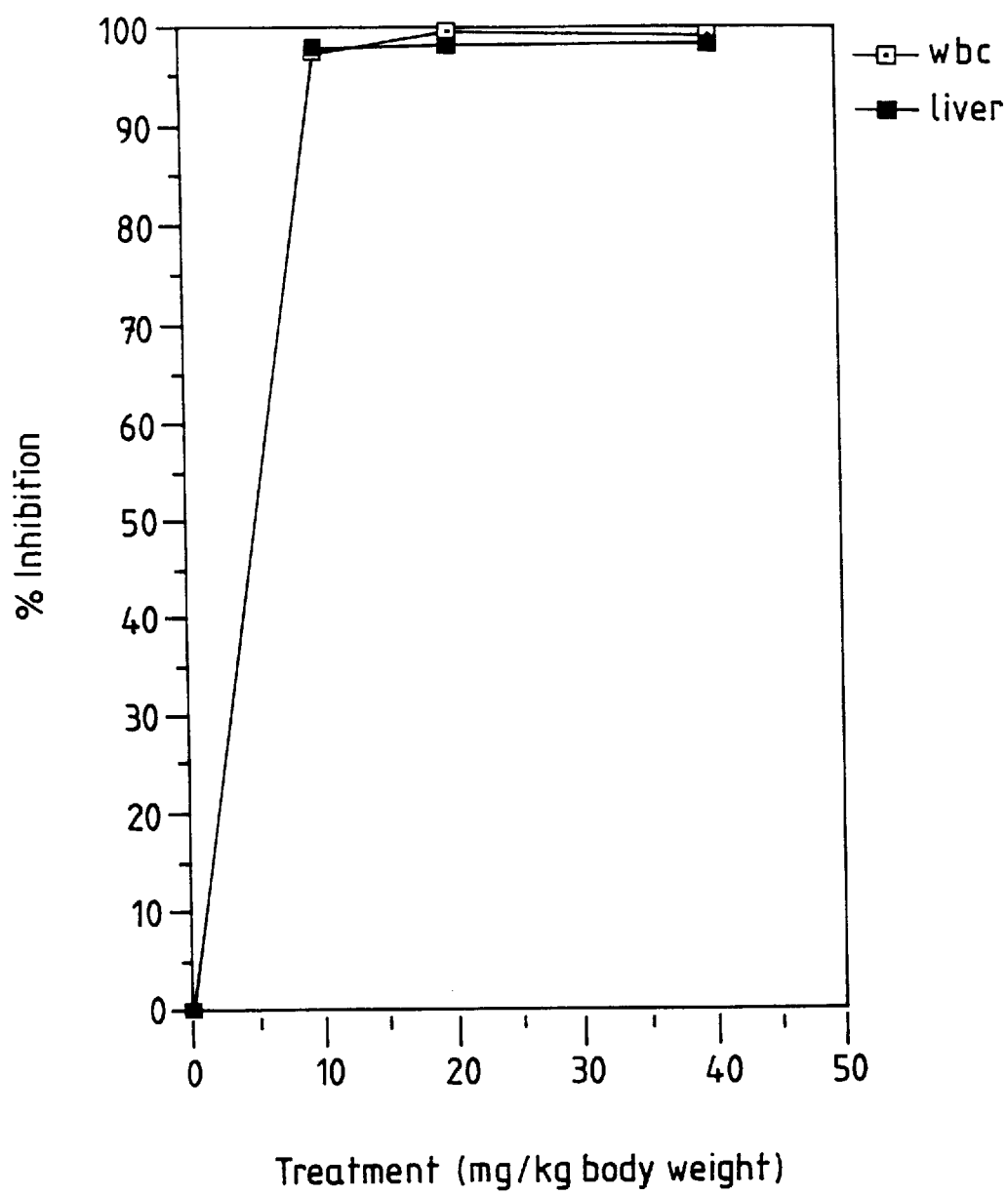
FIG. 19 is a graph of the inhibition of oestrone sulphatase activity in WBC and liver tissue of female Wistar rats two hours following single oral administration of E-Mate (various doses).
Figure 20:
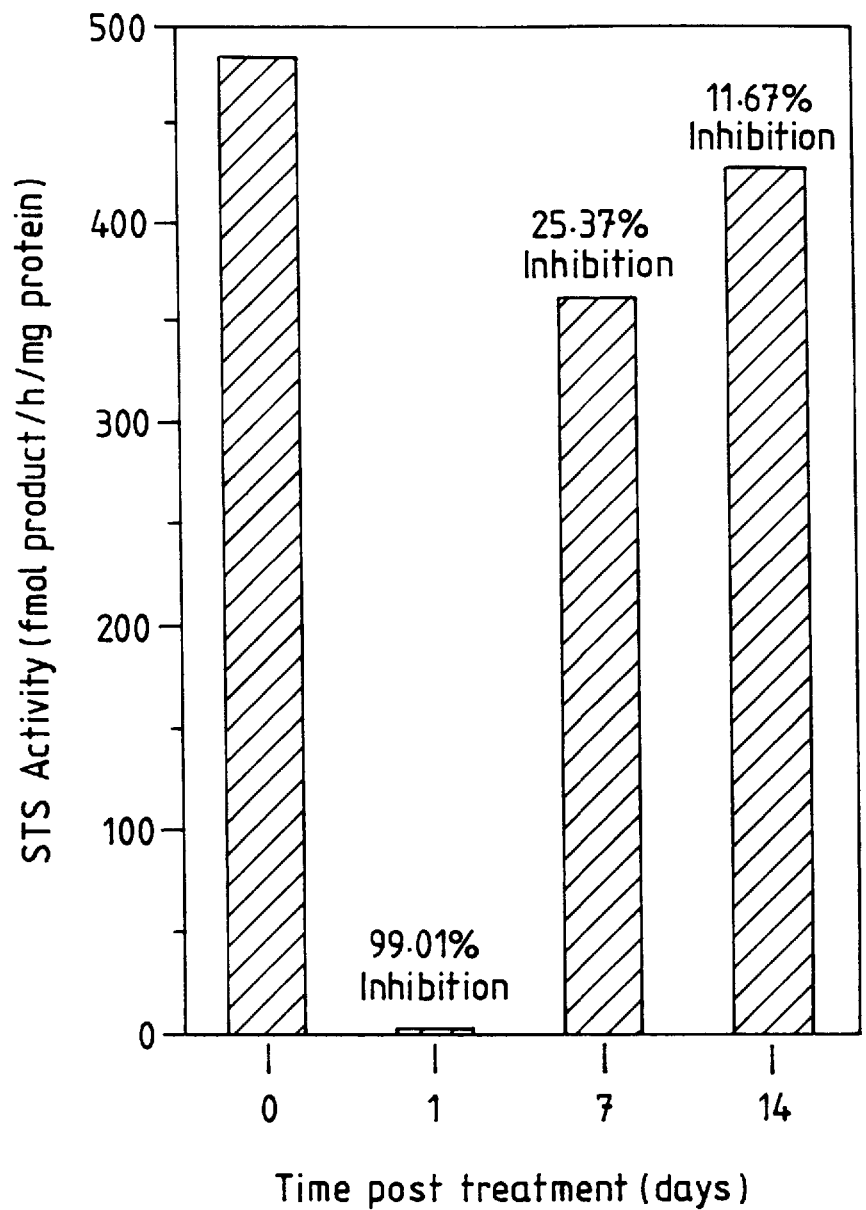
FIG. 20 is a chart of oestrone sulphatase activity in WBC of female Wistar rats at various time intervals following single oral administration of E-Mate (1 mg/kg).
Figure 21:
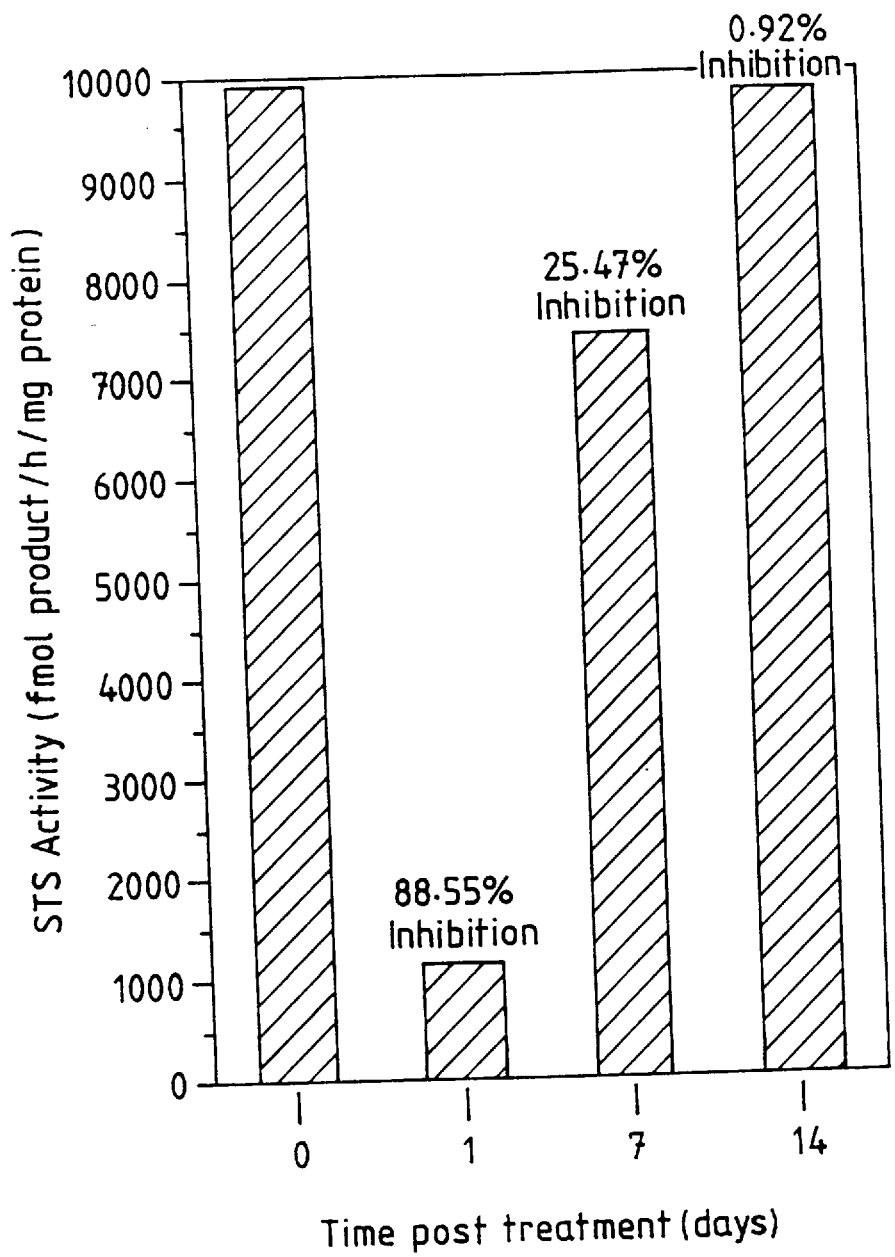
FIG. 21 is a chart of oestrone sulphatase activity in liver tissue of female Wistar rats at various time intervals following single oral administration of E-Mate (1 mg/kg).
Figure 22:
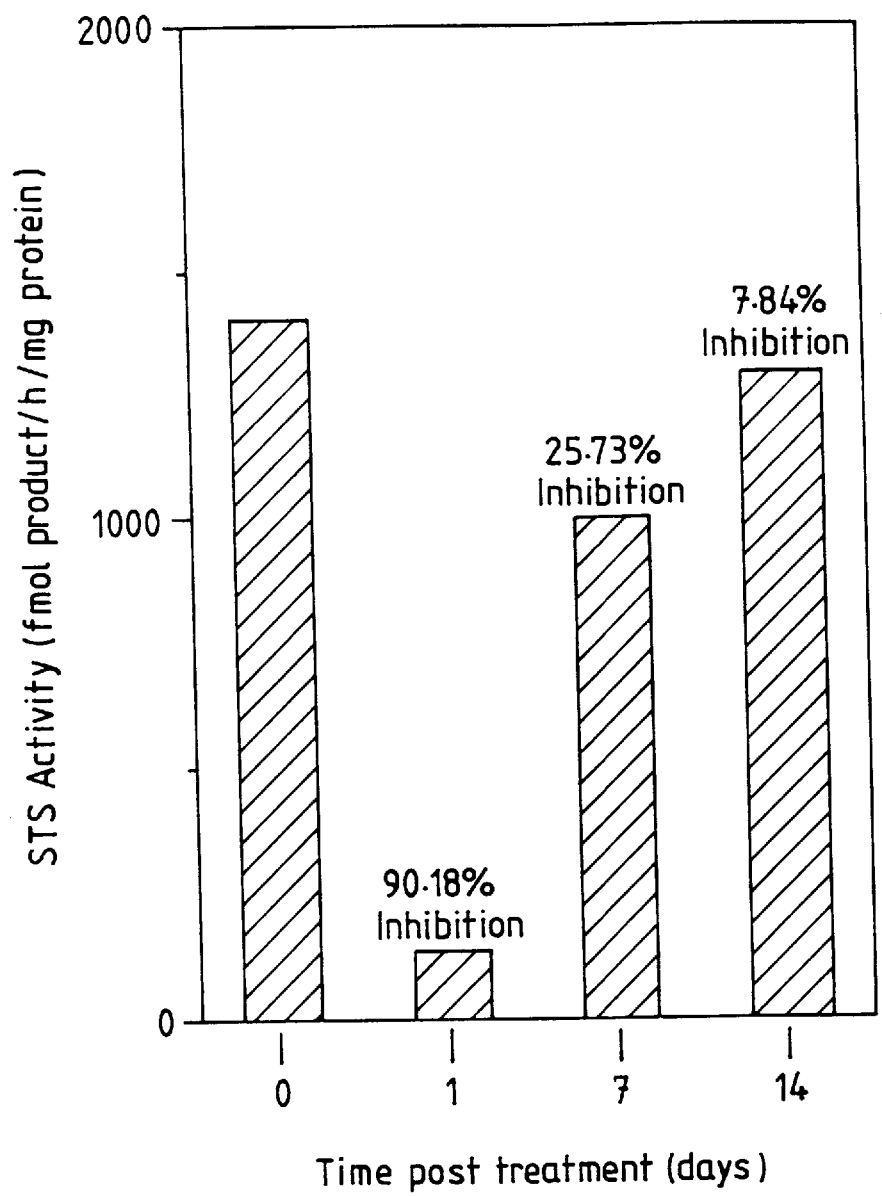
FIG. 22 is a chart of oestrone sulphatase activity in spleen tissue of female Wistar rats at various time intervals following single oral administration of E-Mate (1 mg/kg).
Figure 23:
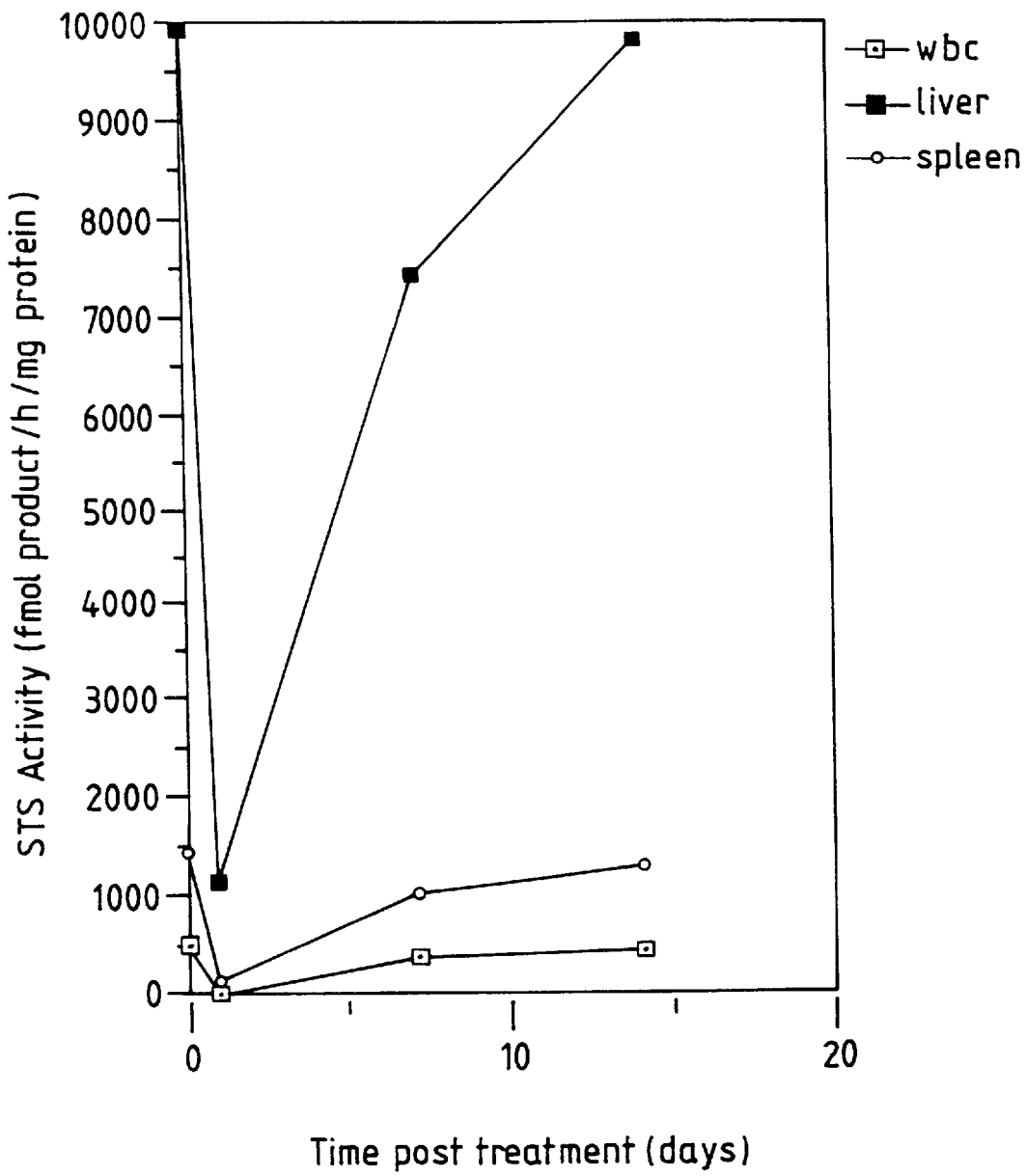
FIG. 23 is a graph of oestrone sulphatase activity in WBC, liver and spleen tissues of female Wistar rats at various time intervals following single oral administration of E-Mate (1 mg/kg).
Figure 24:
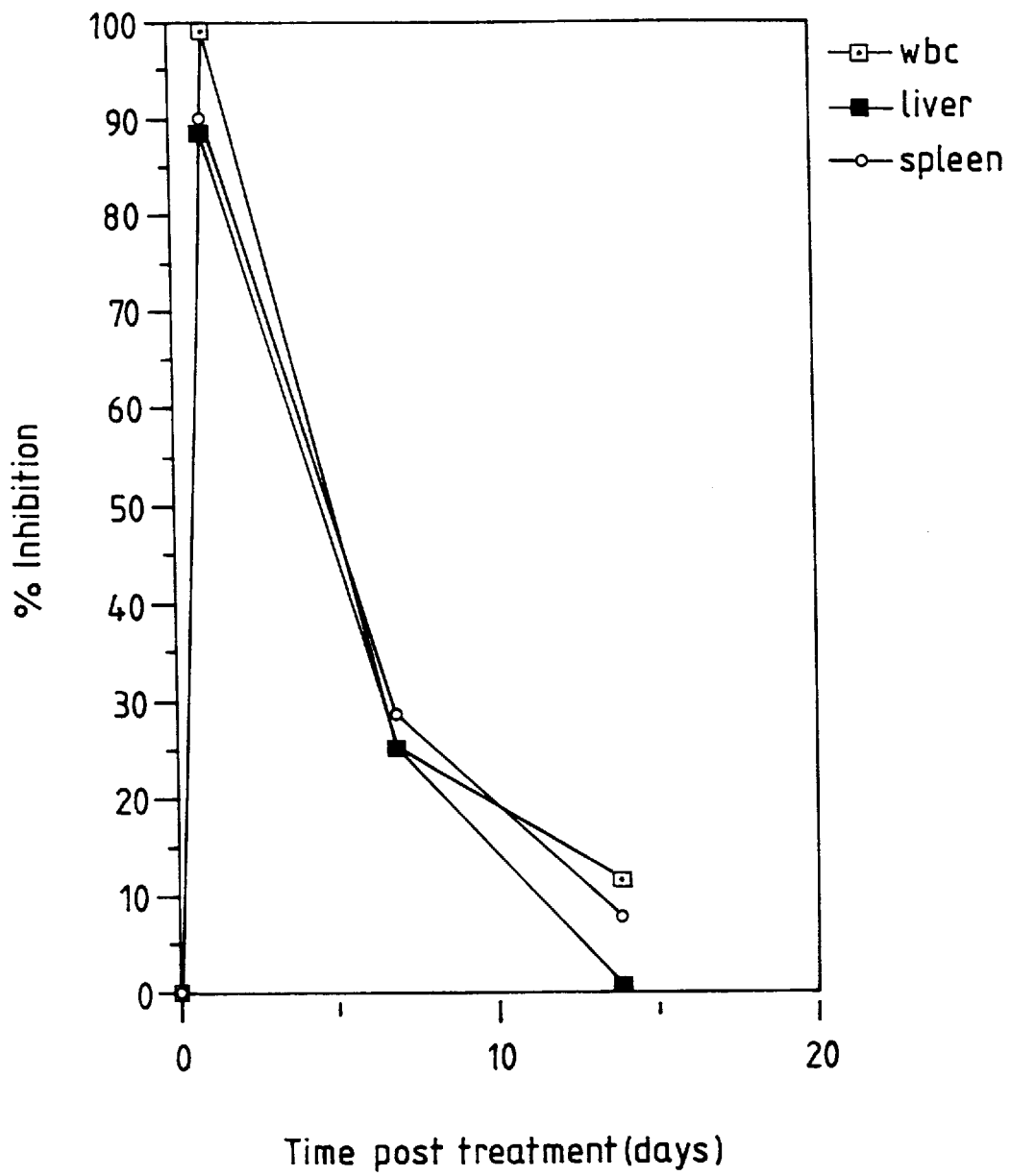
FIG. 24 is a graph of the inhibition of oestrone sulphatase activity in WBC, liver and spleen tissues of female Wistar rats at various time intervals following single oral administration of E-Mate (1 mg/kg).
Figure 25:
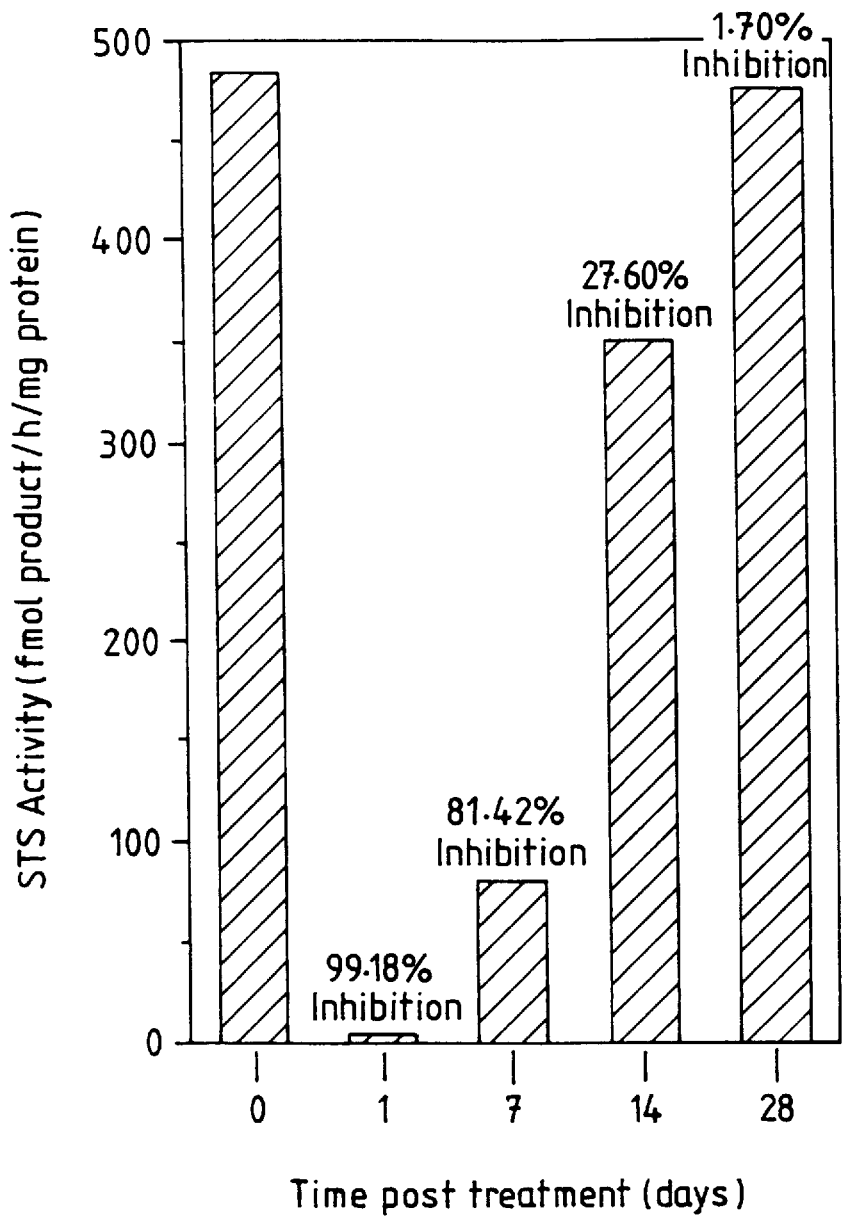
FIG. 25 is a chart of oestrone sulphatase activity in WBC of female Wistar rats at various time intervals following single oral administration of E-Mate (5 mg/kg).
Figure 26:
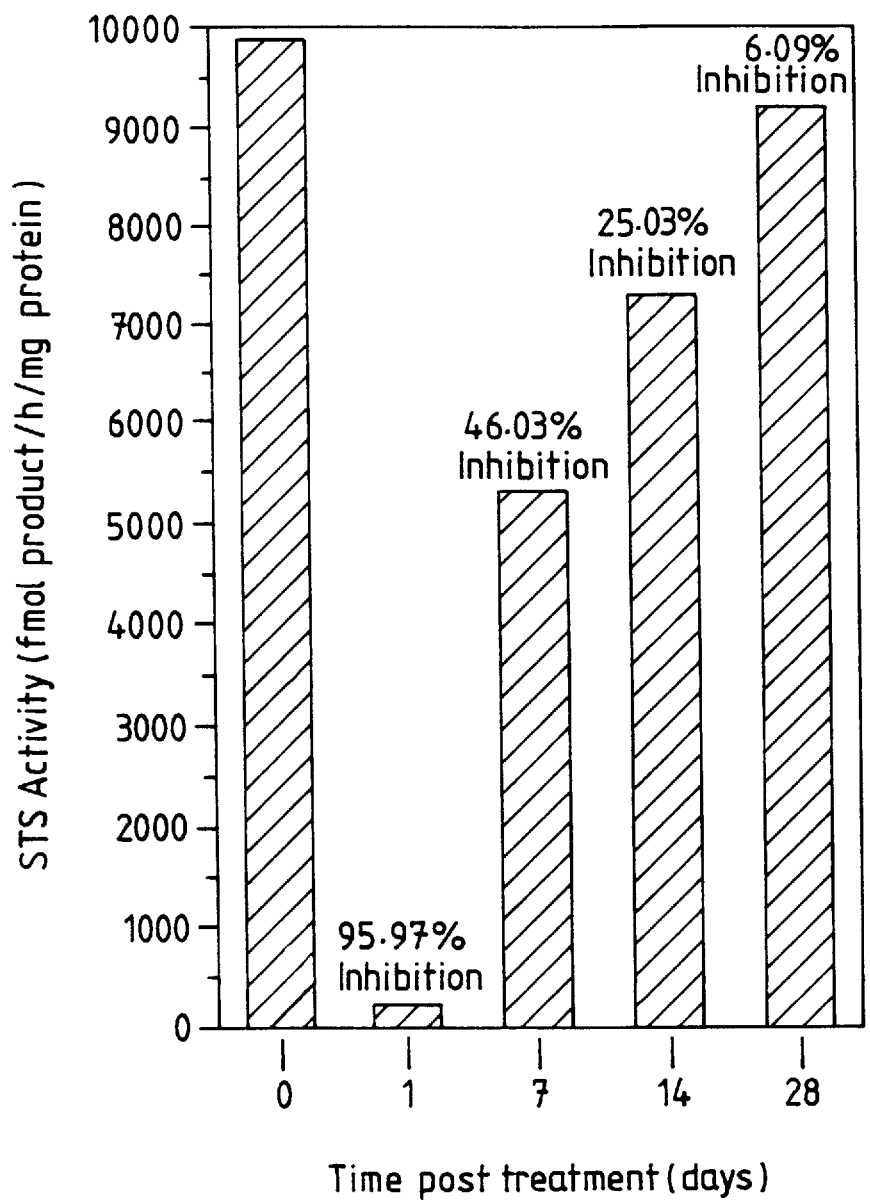
FIG. 26 is a chart of oestrone sulphatase activity in liver tissue of female Wistar rats at various time intervals following single oral administration of E-Mate (5 mg/kg).
Figure 27:
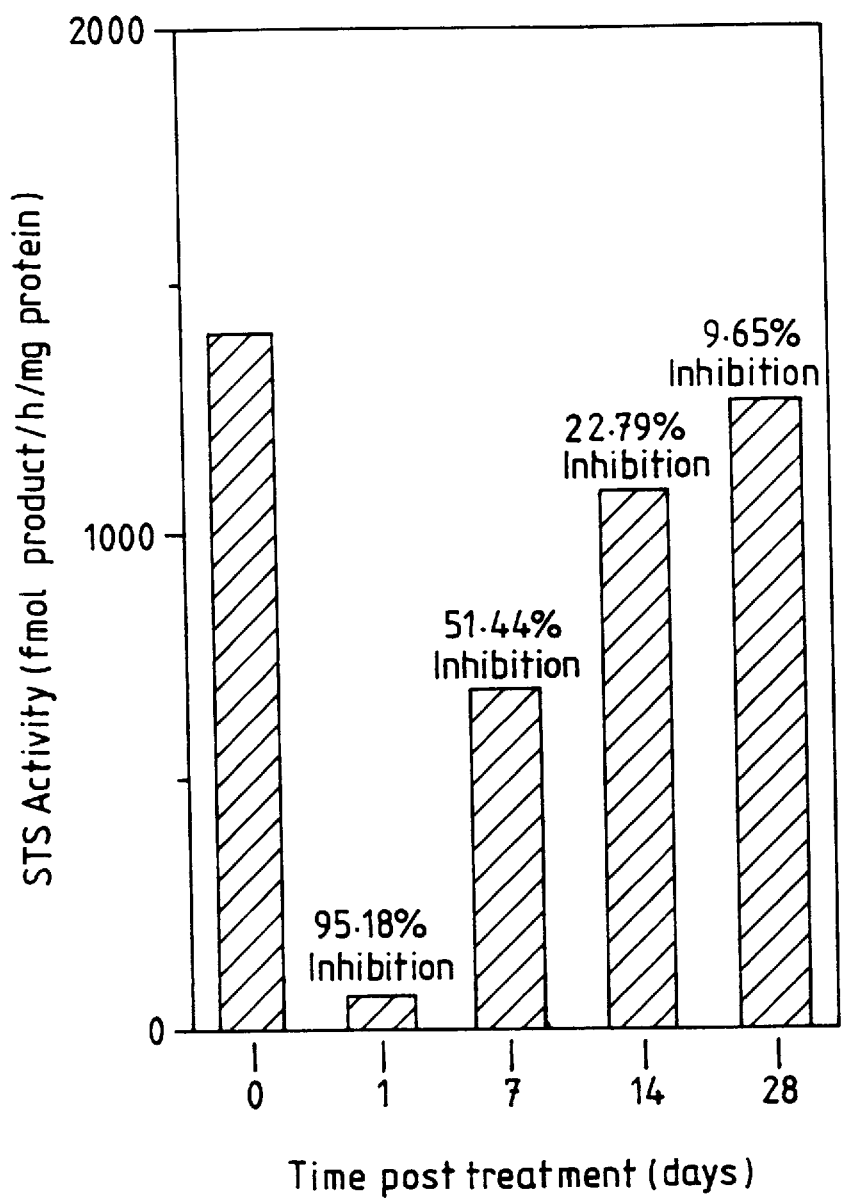
FIG. 27 is a chart of oestrone sulphatase activity in spleen tissue of female Wistar rats at various time intervals following single oral administration of E-Mate (5 mg/kg).
Figure 28:
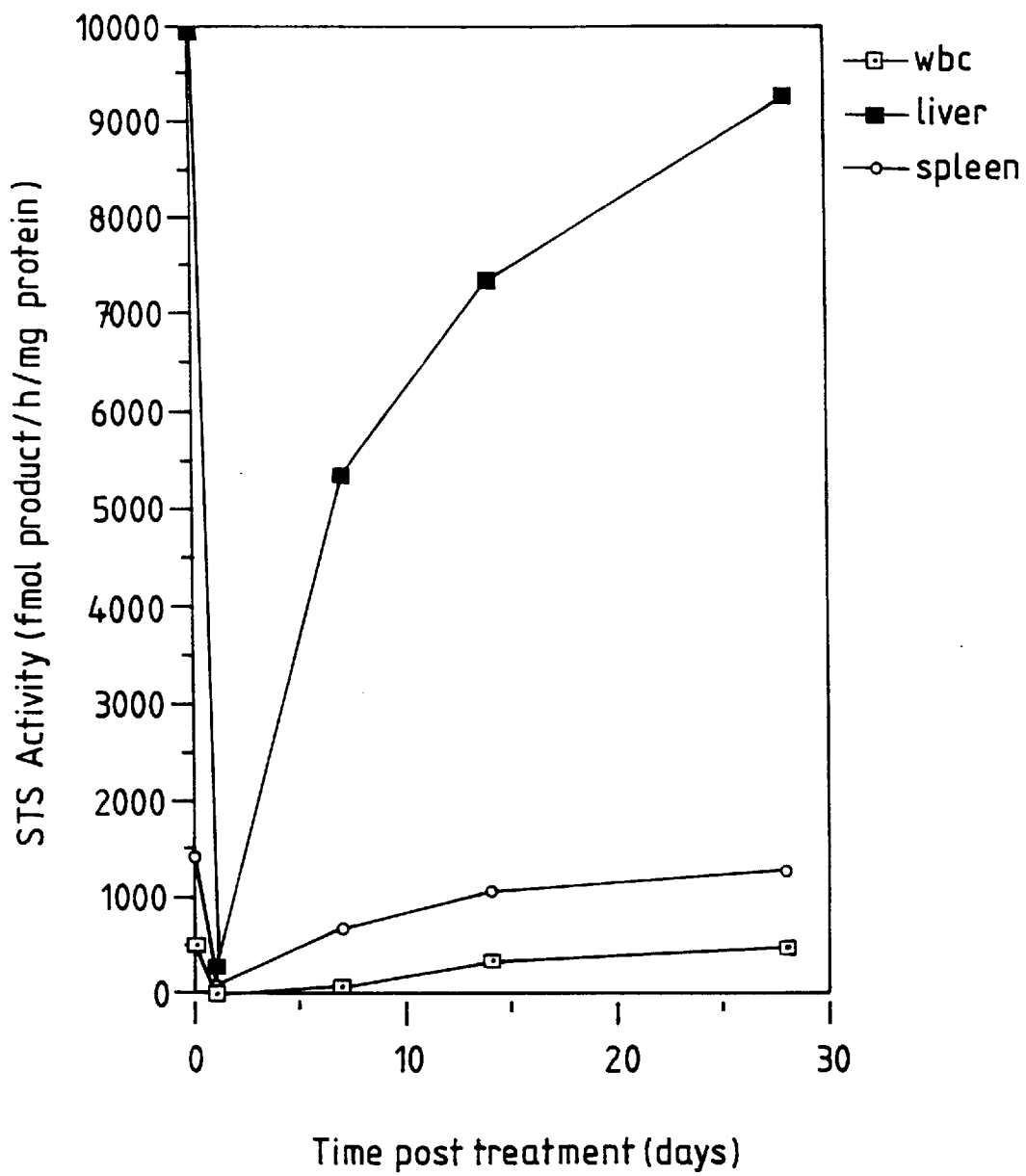
FIG. 28 is a graph of oestrone sulphatase activity in WBC, liver and spleen tissues of female Wistar rats at various time intervals following single oral administration of E-Mate (5 mg/kg).
Figure 29:
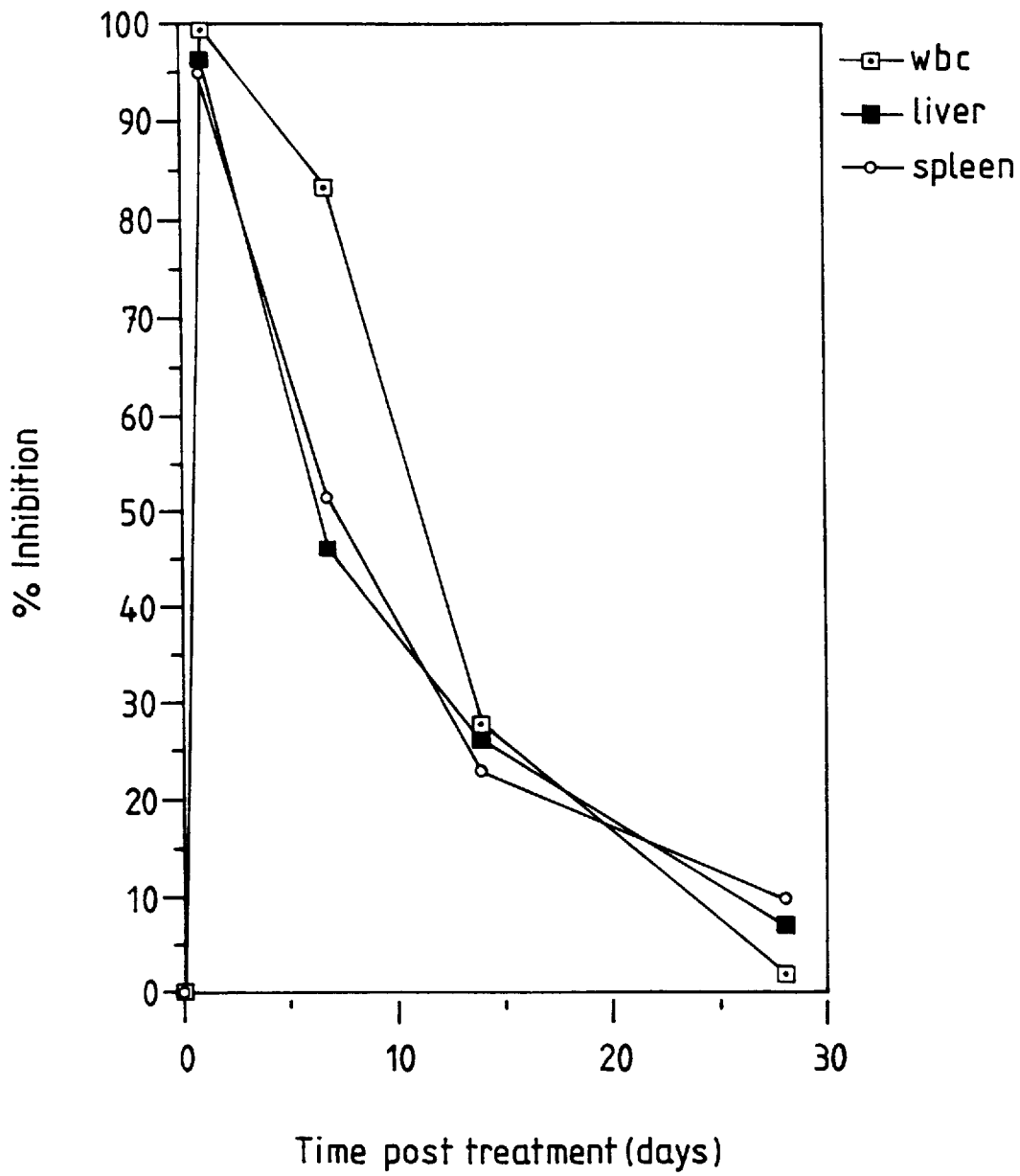
FIG. 29 is a graph of the inhibition of oestrone sulphatase activity in WBC, liver and spleen tissues of female Wistar rats at various time intervals following single oral administration of E-Mate (5 mg/kg).

7. The method of claim 1, wherein the agent is a sulphamate of Formula II shown in FIG. 2*a*.

8. The method of claim 1, wherein the agent is oestrone-3-sulphamate or oestrone-3-N,N-dimethylsulphamate.

* * * * *